| (12) | United States Patent<br>de la Torre et al. | (10) Patent No.: US 9,943,585 B2<br>(45) Date of Patent: Apr. 17, 2018 |
|---|---|---|

(54) METHODS AND COMPOSITIONS RELATED TO REORGANIZATION OF ARENAVIRUS GENOME FOR DEVELOPMENT OF NOVEL ARENAVIRUS LIVE-ATTENUATED VACCINES (LAV)

(71) Applicant: University of Rochester, Rochester, NY (US)

(72) Inventors: Juan Carlos de la Torre, La Jolla, CA (US); Luis Martinez-Sobrido, Rochester, NY (US); Masaharu Iwasaki, La Jolla, CA (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/813,700

(22) Filed: Jul. 30, 2015

(65) Prior Publication Data

US 2016/0206724 A1   Jul. 21, 2016

Related U.S. Application Data

(60) Provisional application No. 62/031,059, filed on Jul. 30, 2014.

(51) Int. Cl.
*A61K 39/12*   (2006.01)
*C12N 7/00*   (2006.01)
*A61K 39/00*   (2006.01)

(52) U.S. Cl.
CPC ............... *A61K 39/12* (2013.01); *C12N 7/00* (2013.01); *A61K 2039/5254* (2013.01); *C12N 2760/10021* (2013.01); *C12N 2760/10034* (2013.01); *C12N 2760/10062* (2013.01)

(58) Field of Classification Search
None
See application file for complete search history.

(56) References Cited

PUBLICATIONS

Martinez-Sobrido et al., Expert Review of Vaccines, 2016, 15(9):1113-1121.*
Cheng et al., Journal of Virology, 2015, 89(14):7373-7384.*
Iwasaka et al., Journal of Virology, 2015, 89(23):12166-12177.*
Lukashevich et al., Expert Review of Vaccines, 2016, 15(9):1135-1150.*
CDC's Arenaviridae document, 2013, 4 page printout available from www.cdc.gov/vhf/virus-families/arenaviridae.html.*
CDC's LCMV factsheet, 2014, 3 page printout available from www.cdc.gov/vhf/lcm/pdf/factsheet.pdf.*

* cited by examiner

*Primary Examiner* — Stacy B Chen
(74) *Attorney, Agent, or Firm* — Meunier Carlin & Curfman LLC

(57) ABSTRACT

Disclosed are compositions and methods related to recombinant arenaviruses and their use in vaccines for the treatment or prevention of an arenavirus infection.

14 Claims, 11 Drawing Sheets

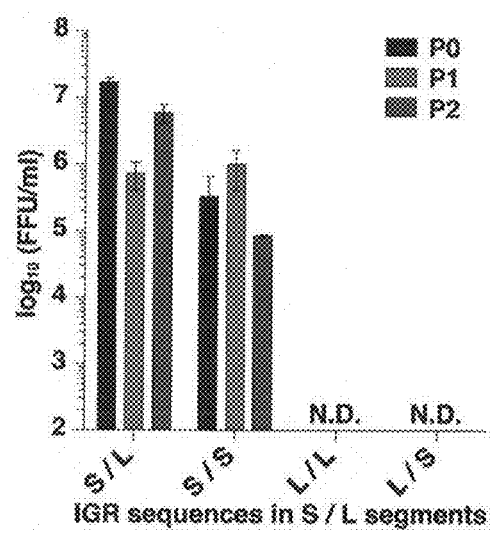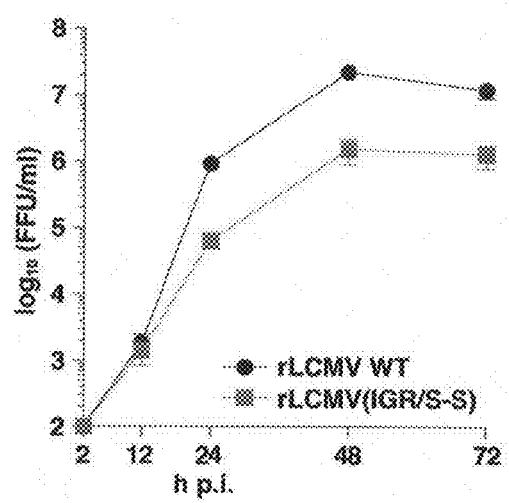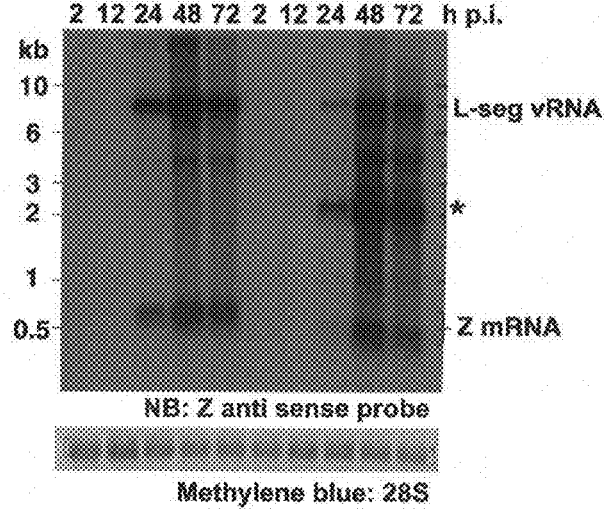

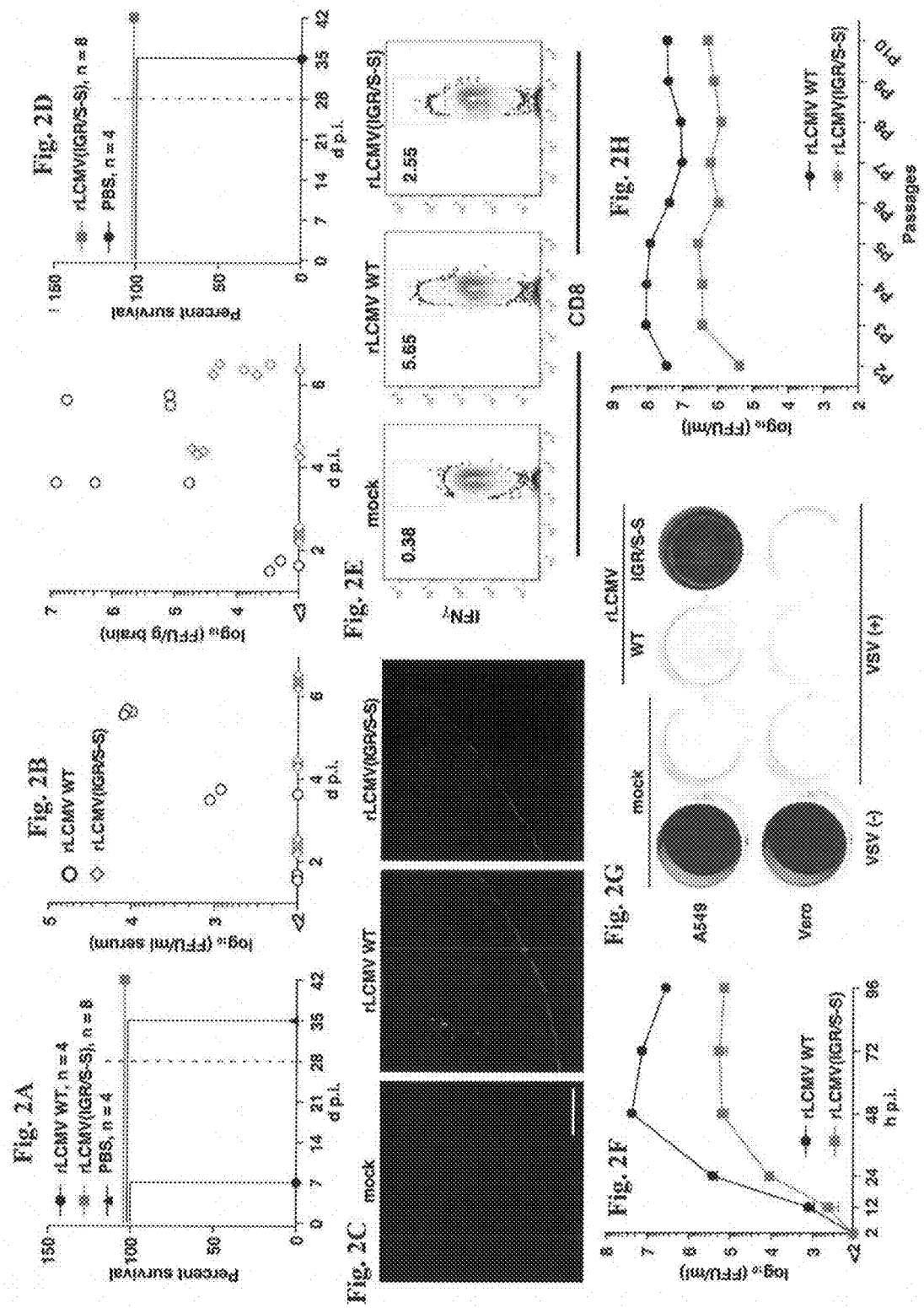

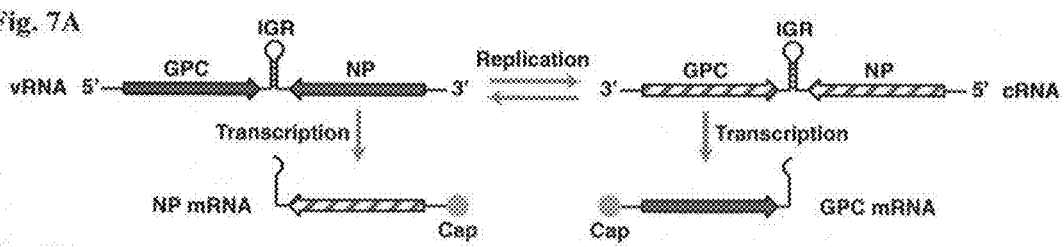
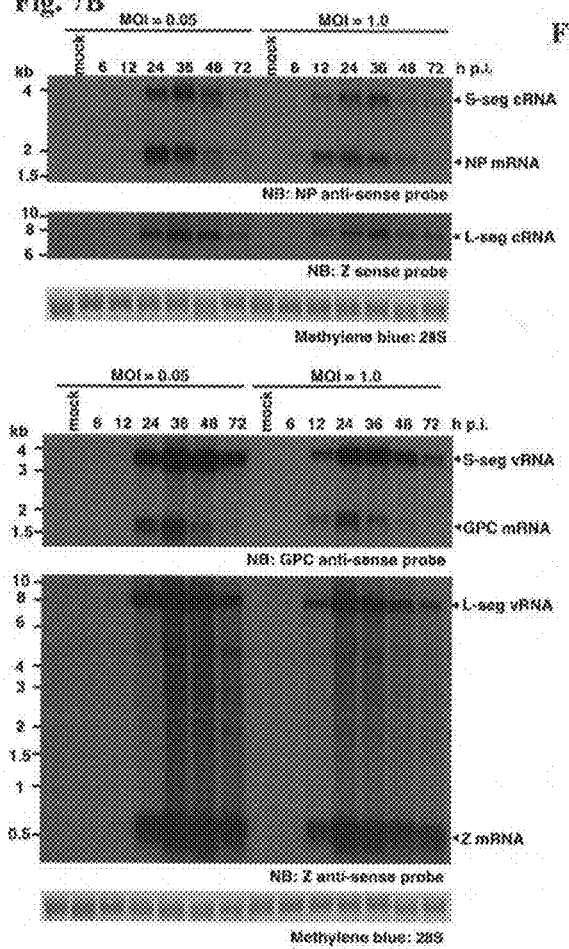
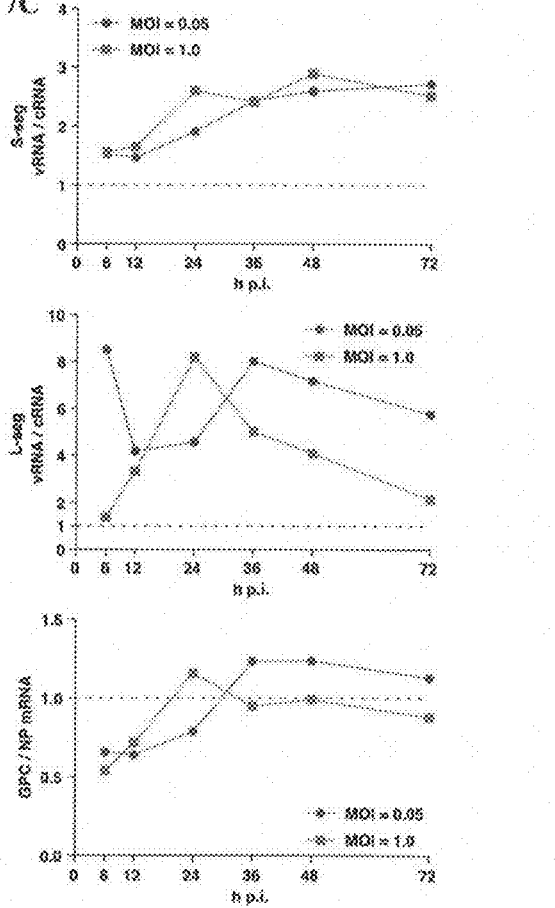

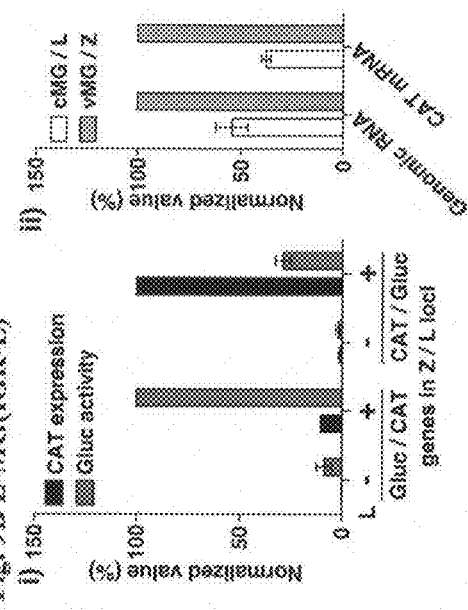
Fig. 9A S-MG(IGR-S)
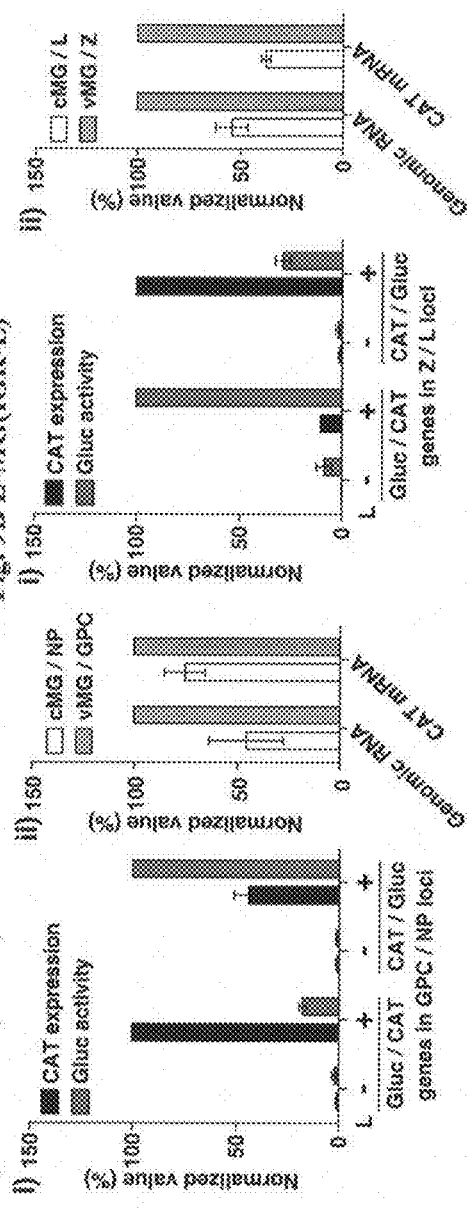
Fig. 9B L-MG(IGR-L)
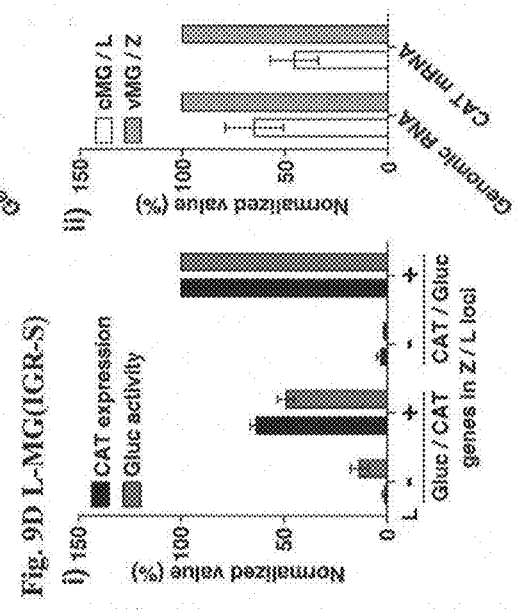
Fig. 9C S-MG(IGR-L)
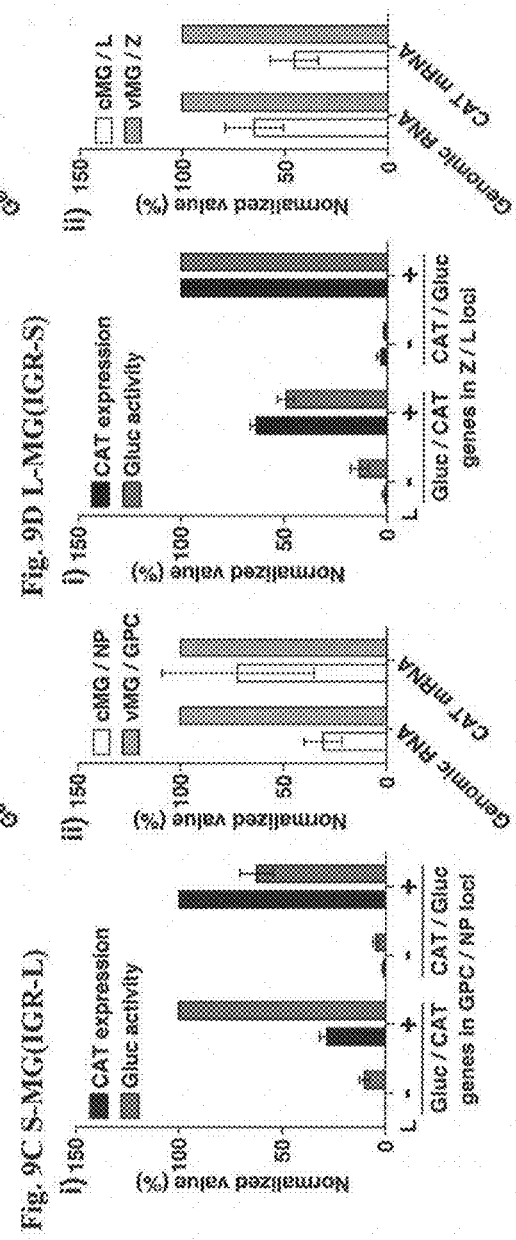
Fig. 9D L-MG(IGR-S)

Fig. 12

METHODS AND COMPOSITIONS RELATED TO REORGANIZATION OF ARENAVIRUS GENOME FOR DEVELOPMENT OF NOVEL ARENAVIRUS LIVE-ATTENUATED VACCINES (LAV)

This application claims the benefit of U.S. Provisional Application No. 62/031,059, which was filed on Jul. 30, 3014 and is incorporated herein by reference in its entirety.

This invention was made with government support under AI047140 awarded by the National Institutes of Health. The government has certain rights in the invention.

I. BACKGROUND

Several arenaviruses, chiefly Lassa virus (LASV), cause hemorrhagic fever disease in humans and pose a great public health concern in their endemic regions. Moreover, evidence indicates that the worldwide-distributed prototypic arenavirus lymphocytic choliomeningitis virus (LCMV) is a neglected human pathogen of clinical significance. What are needed are live attenuated arenavirus vaccines comprising recombinant arenaviruses that 1) grow well in cultured cells, 2) do not exhibit virulence in vivo, and 3) provide protection against a lethal challenge with wild type virus.

II. SUMMARY

Disclosed herein in one aspect are methods and compositions related to recombinant arenaviruses. In one aspect, disclosed herein are recombinant arenaviruses, wherein the intergenic region of the L segment of the viral genome has been substituted with an S segment intergenic region.

In one aspect the S segment intergenic region that has replaced the L segment intergenic region of the disclosed recombinant arenaviruses are derived from a different species of arenavirus than the recombinant virus, the same species of arenavirus as the recombinant virus, or is a synthetic sequence with S-like features.

In one aspect disclosed herein are live attenuated arenavirus vaccine comprising the recombinant arenavirus of any preceding aspect.

Also disclosed are methods of immunizing a subject against an arenavirus infection comprising administering to the subject the recombinant arenavirus of any preceding aspect.

In one aspect, also disclosed herein are methods of attenuating an arenavirus comprising substituting the L segment intergenic region of the arenavirus with an S segment intergenic region.

In one aspect, disclosed herein are arenavirus vaccines comprising a recombinant arenavirus, wherein the L segment intergenic region of the recombinant arenavirus has been substituted with an S segment intergenic region.

Also disclosed are methods of immunizing a subject against an arenavirus infection comprising administering to the subject a recombinant arenavirus, wherein the L segment intergenic region of the recombinant arenavirus has been substituted with an S segment intergenic region.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1A shows the generation of rLCM viruses with different IGR combinations. FIG. 1A shows a comparison of S and L IGRs predicted structures. Secondary structures of genome (vRNA) (SEQ ID NO: 1) and antigenome (cRNA) (SEQ ID NO: 2) S and genome (vRNA) (SEQ ID NO: 3) and antigenome (cRNA) (SEQ ID NO: 4) L IGRs were determined using CentroidFold.

FIGS. 1B, 1C, and 1D show the generation of rLCM viruses with different IGR combinations. FIG. 1B shows the rescue of rLCMV with different IGR combinations. BHK-21 cells were transfected with pol-I plasmids expressing S and L RNA genome species containing the indicated IGR combination, together with plasmids expressing the viral trans-acting factors NP and L. Tissue culture supernatants (TCS) from transfected cells were collected and virus titers determined (P0). P0-TCS were used to infect fresh BHK-21 cells and 72 h later TCS (P1) were collected, their virus titers determined, and used to infect fresh BHK-21 cells (P2). N.D., not detected. FIG. 1C shows growth kinetics of rLCMV(IGR/S-S). BHK-21 cells were infected (moi=0.01) with P2-TCS of either rLCMV or rLCMV(IGR/S-S). At the indicated h p.i., TCS were collected and virus titers determined. FIG. 1D shows the characterization of viral RNA synthesis. At the same time points as in (C), total cellular RNA was isolated and examined by Northern Blotting using a Z anti-sense probe. 28S ribosomal RNA (28S) was detected by methylene blue staining. Data represent means±SD of triplicate samples.

FIGS. 2A, 2B, 2C, 2D, 2E, 2F, 2G, and 2H show the attenuation, protective properties and stability of rLCMV (IGR/S-S). FIGS. 2A-C show that rLCMV(IGR/S-S) is highly attenuated in vivo and induces protection against a lethal challenge with WT LCMV. Six week-old B6 mice were infected with rLCMV WT or rLCMV(IGR/S-S) using $10^3$ FFU, i.c. FIG. 2A shows that at 28 days p.i. (broken line), mice that survived were subjected to a lethal challenge with WT LCMV ($10^3$ FFU, i.c.). FIG. 2B shows that virus titers in serum or brain were determined at the indicated days p.i. (rLCMV WT, N=3 per time point; rLCMV(IGR/S-S), N=5 or 6 per time point). FIG. 2C shows the detection of viral antigen (NP, red) in brain at 6 days p.i. by IF. Cell nuclei were visualized by DAPI staining (blue). Bar, 200 μm. FIGS. 2D and 2E show that immunization with rLCMV (IGR/S-S) induces protection against a lethal LCMV challenge. Mice were infected ($10^5$ FFU, i.p.) with rLCMV WT or rLCMV(IGR/S-S), or mock-infected (PBS). At 28 days p.i. (broken line), mice were subjected to a lethal LCMV challenge ($10^3$ FFU, i.c.) (D) or LCMV-specific CD8 T-cells in the spleen of immunized mice were examined for cytokine production by flow cytometry (E). FIG. 2F shows the growth kinetics of rLCMV(IGR/S-S) in IFN competent cells. A549 cells were infected with either rLCMV or rLCMV(IGR/S-S) (moi=0.01). Virus titers in TCS were determined at the indicated h p.i. Data represent means±SD of triplicate samples. FIG. 2G shows that rLCMV(IGR/S-S) did not inhibit IFN-I production. A549 or Vero cells were infected with rLCMVs (moi=0.1) or remained uninfected (mock), and 24 h later cells were infected with VSV (moi=0.01, VSV(+)) or remained uninfected (VSV(−)). At 48 h p.i. with VSV cells were fixed and stained with crystal violet. FIG. 2H shows the stability of IGR-mutated LCMVs. BHK-21 cells were infected with either rLCMV WT or rLCMV(IGR/S-S) (moi=0.01). At 72 h p.i. TCS was collected and used to infect fresh BHK-21 cells (moi=0.01); this process was serially repeated throughout passages P2 to P10. Virus titers in TCS were determined for each passage.

FIG. 3 shows that rLCMV(IGR/S-S) does not sustain long term infection in mice. Two adult B6 mice were infected i.p. with rLCMV(IGR/S-S) (1×105 FFU). Six weeks later, total RNA was extracted from indicated organs and subjected to RT-PCR for the detection of NP and GAPDH. RNA sample from rLCMV(IGR/S-S)-infected BHK-21 cells (P10) and DEPC H2O were used for positive (+) and negative (−) controls, respectively.

FIG. 4 shows that mice immunized with rLCMV(IGR/S-S) elicit CTL response specific to an LCMV T cell epitope. Mice were infected (105 FFU, i.p.) with rLCMV WT or rLCMV(IGR/S-S), or mock-infected (PBS). At 28 days p.i., total number of cytokine-producing GP33-41 LCMV-specific CD8 T-cells in the spleen was analyzed by flow cytometoly. Data represent means±SD. One of representative dot plot data was shown in FIG. 2E.

FIG. 5 shows that rLCMV(IGR/S-S) was incapable of inhibiting IFN induction. VSV titers in TCS at 32 h after VSV infection in FIG. 2G were determined by a plaque assay. Data represent means±SD of triplicate samples.

FIG. 6 shows the S-IGR (SEQ ID NO: 1) sequence within the L segment of rLCMV(IGR/S-S) was genetically stable during serial passages. DNA sequence chromatogram of the region containing S-IGR within the S or L segment RNA of RT-PCR product from rLCMV WT—(SEQ ID NO: 5) and rLCMV(IGR/S-S)—(SEQ ID NO: 6) infected cells, respectively, at passage 10 (P10) was analyzed by 4Peaks program.

FIGS. 7A, 7B, and 7C show LCMV RNA synthesis. FIG. 7A shows a schematic diagram of arenavirus RNA replication and gene transcription illustrated for the S genome RNA. FIG. 7B shows that BHK-21 cells were infected with rLCMV WT at an moi of 0.05 or 1.0. At the indicated h p.i., total cellular RNA was isolated and analyzed by Northern Blotting. 28S ribosomal RNA (28S) was detected by methylene blue staining for loading controls. FIG. 7C shows that RNA expression levels were quantified using a phosphorimager.

FIGS. 8A and 8B show schematic diagrams of MG constructs. FIG. 8a shows LCMV T7 MG constructs. LCMV MGs were placed under control of a modified T7 promoter (T7pΔ2G) (4) followed downstream by an additional C residue, the hepatitis delta ribozyme (drz) and T7 RNA polymerase terminator (T7T). The additional C was introduced to allow for the generation of the authentic virus 3'-end (genome polarity) following drz-mediated cleavage of unprocessed MG RNA produced intracellularly by the T7 RNA polymerase (10). The S-3'UTR, S-5'UTR, and S-IGR, and L-3'UTR, L-5'UTR, and L-IGR indicate cis-acting LCMV S and L, respectively, genomic sequences. FIG. 8C shows LCMV Pol1 MG constructs. LCMV MGs were placed under control of murine polymerase I promoter (Pol1p) with a nontemplated G residue (11) followed downstream by murine polymerase I terminator (Pol1t). Nr, residual NP ORF-derived sequence; L1 and L2, linker sequence for cloning.

FIGS. 9A, 9B, 9C, and 9D show the posttranscriptional regulation of viral gene expression by IGR. FIGS. 9A-D show the effect of IGR rearrangement on MG activity. MG assays were performed using MG constructs containing the indicated IGR combinations. MG RNA synthesis was examined by Northern Blotting using a CAT anti-sense riboprobe. RNA expression levels were quantified using phosphorimager. Data represent means±SD of three independent experiments. Highest CAT protein expression or Gluc activity in each experiment was set to 100% and used to normalize the rest of the samples.

FIGS. 10A and 10B show the effect of IGR rearrangement on production of infectious VLPs. Infectious VLP assay was performed using MG constructs containing the indicated IGR. FIG. 10a shows CAT expression of transfected cells. Value of S segment WT MG was set to 100% FIG. 10B shows that to determine normalized values of VLP infectivity, CAT expression of VLP-infected cells was divided by CAT expression of transfected cells. Value of S segment WT MG was set to 1. Data represent means±SD of three independent experiments.

Figure 12:
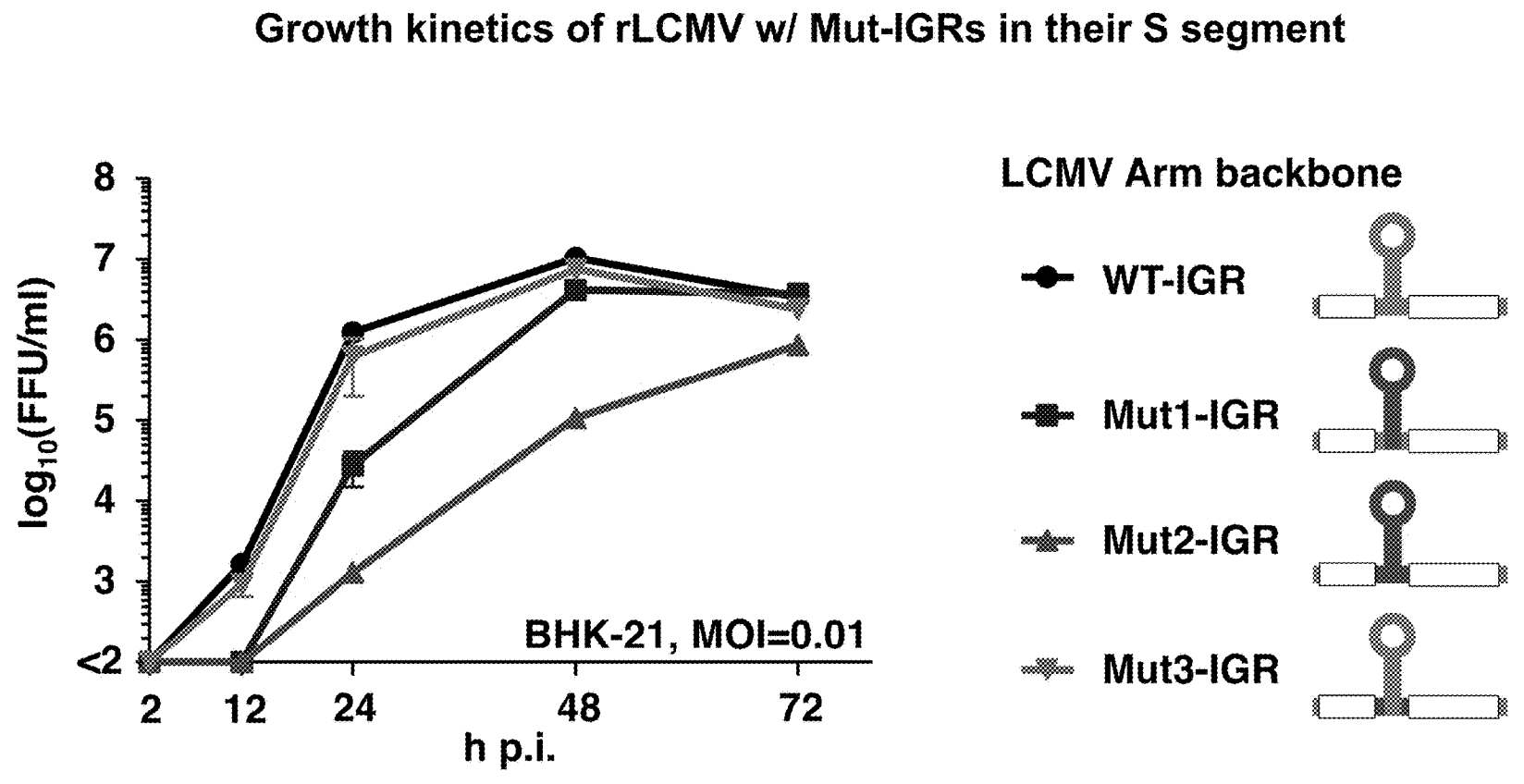

FIG. 12 shows the growth kinetics of rLCMVs with synthetic IGRs.

IV. DETAILED DESCRIPTION

Figure 1A:
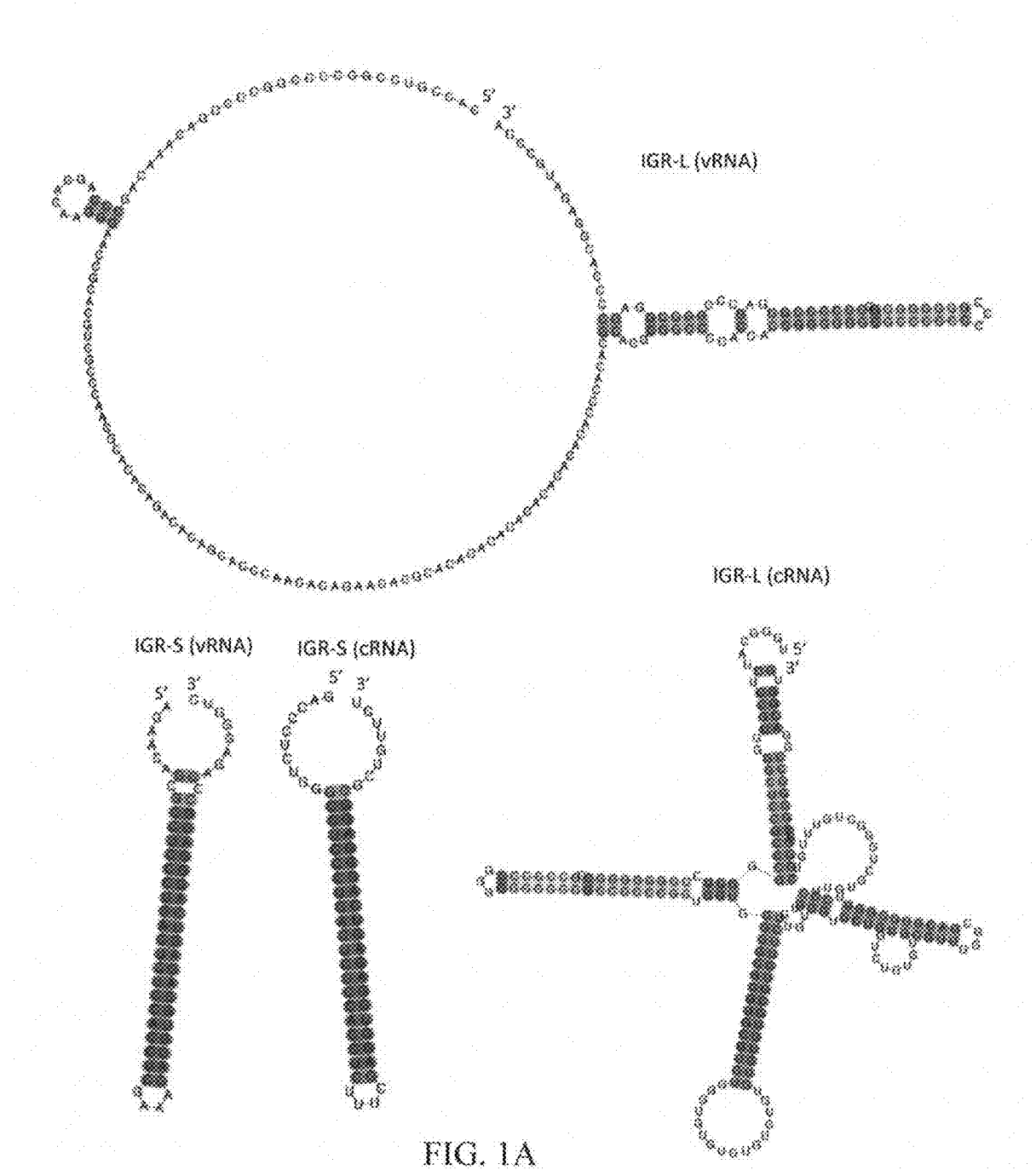

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular recombinant arenavirus is disclosed and discussed and a number of modifications that can be made to a number of molecules including the recombinant arenavirus are discussed, specifically contemplated is each and every combination and permutation of recombinant arenavirus and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Recombinant Arenaviruses

In one aspect, disclosed herein are recombinant arenaviruses. Arenaviruses are enveloped viruses with a bi-segmented negative strand (NS) RNA genome. Each genome RNA segment, L (ca 7.3 kb) and S (ca 3.5 kb), uses an ambisense coding strategy to direct the synthesis of two polypeptides in opposite orientation, separated by a noncoding intergenic region (IGR). The S RNA encodes the viral glycoprotein precursor (GPC) and the nucleoprotein (NP). GPC is post-translationally cleaved by the cellular site 1 protease (SIP) to yield the two mature virion glycoproteins GP1 and GP2 that form the spikes that decorate the virus surface that mediate virus receptor recognition and cell entry. The L RNA encodes the viral RNA dependent RNA polymerase (L polymerase), and the small RING finger protein Z that has functions of a bona fide matrix protein. Herein are described reverse genetics systems for the prototypic arenavirus LCMV, as well as for a variety of arenaviruses including JUNV and LASV. These systems provide a novel and powerful tool for the investigation of the viral cis-acting sequences and proteins, both viral and cellular, that control cell entry, RNA replication, gene expression, assembly and budding of arenaviruses. Each genome segment, S and L, has a distinct IGR.

It is disclosed herein that the generation of a recombinant arenaviruses comprising the S IGR in both the S and L segment results in a virus with optimal properties as: 1) grows well in cultured cells, 2) does not exhibit virulence in vivo, 3) provides protection against a lethal challenge with wild type virus. Thus, in one aspect, disclosed herein are recombinant arenaviruses, wherein the intergenic region of the L segment of the viral genome has been substituted with an S segment intergenic region.

Arenaviruses are currently organized in two genera, Mammarenavirus and Reptarenavirus, which are established to accommodate mammalian and reptilian arenaviruses, respectively, in the same Arenaviridae family. Mammalian arenaviruses are divided into two serogroups based on geographic distribution 1) Old World Arenaviruses which includes lymphocytic choriomeningitis virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, and Wenzhou virus; and 2) New World Arenaviruses which includes Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus.

Accordingly, in one aspect, the disclosed recombinant arenavirus can be an Old World arenavirus or a New World arenavirus. For example, in one aspect, disclosed herein are recombinant arenaviruses wherein the intergenic region of the L segment of the viral genome has been substituted with an S segment intergenic region, and wherein the recombinant arenavirus is an Old World Arenaviruses selected from the group consisting of lymphocytic choriomeningitis virus (LCMV), Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, and Wenzhou virus. Also disclosed are recombinant arenaviruses wherein the intergenic region of the L segment of the viral genome has been substituted with an S segment intergenic region, and wherein the recombinant arenavirus is a New World Arenavirus selected from the group consisting of Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus.

In one aspect, the S-IGR that is substituted for the L segment IGR can be derived from any arenavirus S-IGR. For example, the S-IGR can be derived from Old World Arenaviruses including, but not limited to LCMV (for example, the S-IGR as set forth in SEQ ID NO: 1), Lassa virus (for example, the S-IGR as set forth in SEQ ID NO: 11), Luna virus, Lujo virus (for example, the S-IGR as set forth in SEQ ID NO: 12), Ippy virus, Mopeia virus (for example, the S-IGR as set forth in SEQ ID NO: 13), Mobala virus (for example, the S-IGR as set forth in SEQ ID NO: 14), Merino walk virus, Menekre virus, Morogoro virus, Gbagroube virus, Kodoko virus, Lemniscomys virus, Mus minutoides virus, Lunk virus, Giaro virus, and Wenzhou virus or New World Arenavirus including, but not limited to Tacaribe virus (for example, the S-IGR as set forth in SEQ ID NO: 17), Junin virus (for example, the S-IGR as set forth in SEQ ID NO: 15), Machupo virus (for example, the S-IGR as set forth in SEQ ID NO: 16), Guanarito virus (for example, the S-IGR as set forth in SEQ ID NO: 18), Pichinde virus (for example, the S-IGR as set forth in SEQ ID NO: 19), Flexal virus (for example, the S-IGR as set forth in SEQ ID NO: 21), Latino virus, Chapare virus (for example, the S-IGR as set forth in SEQ ID NO: 20), Amapari virus, Oliveros virus, Cupixi virus, Tamiami virus, Parana virus, Sabia virus, Patawa virus, Pirital virus, Whitewater Arroyo virus (for example, the S-IGR as set forth in SEQ ID NO: 22), Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus (for example, the S-IGR as set forth in SEQ ID NO: 24), or any variant of the disclosed arenavirus S-IGRs having at least 85%, 8%, 87%, 88%, 89%, 90%, 91%, 92%, 93%, 94%, 95%, 96%, 97%, 98%, 99% or more sequence identity with the disclosed or native S-IGR sequence. Where specific S-IGR sequences are provided, specifically contemplated herein are substitutions comprising those exact sequences. For example, a recombinant LCMV virus wherein the L-IGR has been substituted with an LCMV S-IGR specifically contemplates a recombinant LCMV virus wherein the L-IGR has been substituted with SEQ ID NO: 1. It is further contemplated herein that where a particular substitution is provided (e.g., LCMV L-IGR to S-IGR or LCMV L-IGR to Lassa S-IGR) for an embodiment and where a particular S-IGR sequence is provided herein that falls within the S-IGR of the embodiment, disclosed herein is the specific substitution using the provided S-IGR sequence.

As disclosed above, in one aspect, disclosed herein are arenaviruses wherein the L segment IGR has been substituted with an arenavirus S-IGR. It is understood and herein contemplated that the S-IGR that is replacing the L-IGR can be derived from the same species of arenavirus as the recombinant arenavirus (e.g., a recombinant Lassa virus wherein the viral L-IGR has been substituted with a Lassa virus S-IGR). For example disclosed herein are recombinant arenaviruses wherein the IGR of the L genome segment has been substituted with an S-IGR, and wherein the recombinant arenavirus and the arenavirus from which the substituting S-IGR is derived are both LCMV, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Alternatively, it is also disclosed and herein contemplated that the S-IGR that is replacing the L-IGR can be derived from a different species of arenavirus than the recombinant arenavirus (e.g., a recombinant Lassa virus comprising an LCMV S-IGR in the place of the Lassa virus L-IGR). For example, disclosed herein are recombinant arenaviruses wherein the IGR of the L genome segment has been substituted with an S-IGR, wherein the recombinant arenavirus is LCMV virus and the S-IGR is derived from Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Lassa virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Luna virus and the S-IGR is derived from LCMV virus, Lassa virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Lujo virus and the S-IGR is derived from LCMV virus, Luna virus, Lassa virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Ippy virus and the S-IGR is derived from LCMV virus, Luna virus, Lujo virus, Lassa virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Mopeia virus and the S-IGR is derived from LCMV virus, Luna virus, Lujo virus, Ippy virus, Lassa virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Mobala virus and the S-IGR is derived from LCMV virus, Luna virus, Lujo virus, Ippy virus, Mopeia virus, Lassa virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Merino walk virus and the S-IGR is derived from LCMV virus, Luna virus, Lujo virus, Ippy virus, Mopeia virus, Mobala virus, Lassa virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Menekre virus and the S-IGR is derived from LCMV virus, Luna virus, Lujo virus, Ippy virus, Mopeia virus, Mobala virus, Merino walk virus, Lassa virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Morogoro virus and the S-IGR is derived from LCMV virus, Luna virus, Lujo virus, Ippy virus, Mopeia virus, Mobala virus, Merino walk virus, Menekre virus, Lassa virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Gbagroube virus and the S-IGR is derived from LCMV virus, Luna virus, Lujo virus, Ippy virus, Mopeia virus, Mobala virus, Merino walk virus, Menekre virus, Morogoro virus, Lassa virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Kodoko virus and the S-IGR is derived from LCMV virus, Luna virus, Lujo virus, Ippy virus, Mopeia virus, Mobala virus, Merino walk virus, Menekre virus, Morogoro virus, Gbagroube virus, Lassa virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Lemniscomys virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lassa virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Mus minutoides virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Lassa virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Lunk virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lassa virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Giaro virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Lassa virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Wenzhou virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Lassa virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Junin virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Machupo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Tacaribe virus and the S segment IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Guanarito virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment has been substituted with an S-IGR, wherein the recombinant arenavirus is Pichinde virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Flexal virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Pichinde virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Latino virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Pichinde virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Chapare virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Pichinde virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Amapari virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Pichinde virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Oliveros virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Pichinde virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Cupixi virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Pichinde virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Tamiami virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Pichinde virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Parana virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Pichinde virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Sabia virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Pichinde virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Patawa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Pichinde virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Pirital virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pichinde virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Whitewater Arroyo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Pichinde virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Pampa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pichinde virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Bear canyon virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Pichinde virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Tonto Creek virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Pichinde virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Allpahuayo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Pichinde virus, Catarina virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Catarina virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Skinner Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Catarina virus, Real de Catorce virus, Big Brushy Tank virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Real de Catorce virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Big Brushy Tank virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Big Brushy Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Catarina virus, or Ocozocoautla de Espinosa virus.

Also, for example, disclosed herein are recombinant arenaviruses wherein the IGR of the L genome segment of the viral genome has been substituted with an S-IGR, wherein the recombinant arenavirus is Ocozocoautla de Espinosa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, or Catarina virus.

In one aspect, both the recombinant arenavirus and the virus from which the S-IGR that replaced the L-IGR is derived are both Old World Arenaviruses or both New World Arenaviruses. Also disclosed are examples where the recombinant arenavirus is an Old World Arenavirus and the S-IGR is derived from a New World Arenavirus. Also disclosed are examples where the recombinant arenavirus is a New World Arenavirus and the S-IGR is derived from an Old World Arenavirus.

It is also disclosed and herein contemplated that the S-IGR that is replacing the L-IGR can be synthetically derived. That is, the substituting S-IGR is a synthetic sequence with S-like features. Thus, for example, disclosed herein are recombinant arenaviruses wherein the IGR of the L genome segment has been substituted with a synthetic sequence comprising S-IGR-like features. In one aspect, the synthetic IGR can be a synthetic IGR as shown in FIGS. 11 and 12 and as set forth in SEQ ID NO: 7 (Mut1), SEQ ID NO: 8 (Mut2), SEQ ID NO: 9 (Mut3), and/or SEQ ID NO: 28 (Ssyn2) or a variant thereof having at least 85%, 8%, 87%, 88%, 89%, 90%, 91%, 92%, 93%, 94%, 95%, 96%, 97%, 98%, 99% or more sequence identity, wherein any variant is not a naturally occurring S IGR sequence.

It is also contemplated that any of the recombinant viruses disclosed herein can further comprise additional mutations, substitutions, deletions of the viral genome including, but not limited to removal of one or more T cell epitopes, such as, for example, immunodominant and/or subdominant CD8+ T cell epitopes.

Also contemplated is an isolated nucleic acid segment which defines an arenavirus genomic L segment which contains the S-IGR sequence in place of the L-IGR sequence as described herein. Further contemplated is a live attenuated virus according to the present disclosure in the form of a virus particle that is the active component of a LAV, or as a suspension of said live virus particles. Also disclosed are cells produced by the process of infecting the cell with any of the disclosed recombinant viruses.

It is understood and herein contemplated that the disclosed recombinant arenaviruses can be used to make a therapeutic or prophylactic vaccine against an arenaviral infection or condition such as a hemorrhagic fever caused by an arenavirus. In one aspect, disclosed herein are methods of immunizing a subject against an arenavirus infection comprising administering to the subject the recombinant arenavirus.

2. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

3. Nucleic Acids

There are a variety of molecules disclosed herein that are nucleic acid based, including for example the nucleic acids that encode, for example an arenavirus S-IGR, as well as various functional nucleic acids. The disclosed nucleic acids are made up of for example, nucleotides, nucleotide analogs, or nucleotide substitutes. Non-limiting examples of these and other molecules are discussed herein. It is understood that for example, mRNA produced in cells transfected with a vector will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_n$O]$_m$CH$_3$, —O$(CH_2)_n$OCH$_3$, —O$(CH_2)_n$NH$_2$, —O$(CH_2)_n$CH$_3$, —O$(CH_2)_n$—ONH$_2$, and —O$(CH_2)_n$ON[$(CH_2)_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., Ann. N.Y. Acad. Sci., 1992, 660, 306-309; Manoharan et al., *Bioorg. Med. Chem. Let.*, 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylaminocarbonyl-oxycholesterol moiety (Crooke et al., *J. Pharmacol. Exp. Ther.,* 1996, 277, 923-937.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Examples are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line that lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells that were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells that have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

5. Live Attenuated Arenavirus Vaccines

The present disclosure describes recombinant areanviruses. One use of the disclosed recombinant arenaviruses is as a component of a live-attenuated vaccine (LAV). Thus, in one aspect the present disclosure also provides for an LAV that is based on the generation of a recombinant LCMV containing the S-IGR in both the S and L segment which is used in the preparation of a live virus with optimal properties as LAV, and having the following characteristics: (1) LAV grows well in cultured cells, (2) LAV does not exhibit virulence in vivo, and (3) LAV provides protection against a lethal challenge with wild type LCMV. In addition, the invention contemplates substitutions of the S-IGR between species of arenavirus to form a useful LAV. Thus, in one aspect, disclosed herein is a live attenuated arenavirus vaccine comprising any of the recombinant arenavirus disclosed herein. Stated more simply, in one aspect, disclosed herein are live attenuated arenavirus vaccines comprising a recombinant arenavirus, wherein the L-IGR of the recombinant arenavirus has been substituted with an S-IGR.

It is understood and herein contemplated that the recombinant arenavirus used in the disclosed live attenuated arenavirus vaccines can be an Old World arenavirus or a New World arenavirus. For example, in one aspect, disclosed herein are live attenuated arenavirus vaccines comprising at least one recombinant arenavirus wherein the IGR of the L genome segment has been substituted with an S-IGR, and wherein the recombinant arenavirus is an Old World arenaviruses selected from the group consisting of lymphocytic choriomeningitis virus (LCMV), Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, and Wenzhou virus. Also disclosed are live attenuated arenavirus vaccines comprising recombinant arenaviruses wherein the L-IGR has been substituted with an S-IGR, and wherein the recombinant arenavirus is a New World arenavirus selected from the group consisting of Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus.

As discussed herein, the live attenuated vaccines of the disclosure comprise recombinant arenaviruses wherein the L-IGR has been substituted with an S-IGR. It is understood and herein contemplated that the S-IGR that is replacing the L-IGR can be derived from the same species of arenavirus as the recombinant arenavirus (e.g., a recombinant Lassa virus wherein the viral L-IGR has been substituted with a Lassa virus S-IGR). For example disclosed herein are recombinant arenaviruses wherein the L-IGR has been substituted with an S-IGR, and wherein the recombinant arenavirus and the arenavirus from which the substituting S-IGR are both lymphocytic choriomeningitis virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Alternatively, it is also disclosed and herein contemplated that live attenuated arenavirus vaccines comprise recombinant arenaviruses wherein the L-IGR of the recombinant arenavirus has been substituted with an S-IGR, and that the S-IGR that is replacing the L-IGR can be derived from a different species of arenavirus than the recombinant arenavirus (e.g., a recombinant Lassa virus comprising an LCMV S-IGR in the place of the Lassa virus L-IGR). For example, disclosed herein are live attenuated arenavirus vaccines comprising a recombinant arenavirus wherein the L-IGR has been substituted with an S-IGR, wherein the recombinant arenavirus is LCMV virus and the S-IGR is derived from Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Lassa virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Luna virus and the S-IGR is derived from LCMV virus, Lassa virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Lujo virus and the S-IGR is derived from LCMV virus, Luna virus, Lassa virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Ippy virus and the S-IGR is derived from LCMV virus, Luna virus, Lujo virus, Lassa virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Mopeia virus and the S-IGR is derived from LCMV virus, Luna virus, Lujo virus, Ippy virus, Lassa virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Mobala virus and the S-IGR is derived from LCMV virus, Luna virus, Lujo virus, Ippy virus, Mopeia virus, Lassa virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Merino walk virus and the S-IGR is derived from LCMV virus, Luna virus, Lujo virus, Ippy virus, Mopeia virus, Mobala virus, Lassa virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Menekre virus and the S-IGR is derived from LCMV virus, Luna virus, Lujo virus, Ippy virus, Mopeia virus, Mobala virus, Merino walk virus, Lassa virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Morogoro virus and the S-IGR is derived from LCMV virus, Luna virus, Lujo virus, Ippy virus, Mopeia virus, Mobala virus, Merino walk virus, Menekre virus, Lassa virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Gbagroube virus and the S-IGR is derived from LCMV virus, Luna virus, Lujo virus, Ippy virus, Mopeia virus, Mobala virus, Merino walk virus, Menekre virus, Morogoro virus, Lassa virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Kodoko virus and the S-IGR is derived from LCMV virus, Luna virus, Lujo virus, Ippy virus, Mopeia virus, Mobala virus, Merino walk virus, Menekre virus, Morogoro virus, Gbagroube virus, Lassa virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Lemniscomys virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lassa virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Mus minutoides virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Lassa virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Lunk virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lassa virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Giaro virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Lassa virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Wenzhou virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Lassa virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Junin virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Machupo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Tacaribe virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Guanarito virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Pichinde virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Flexal virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Pichinde virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Latino virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Pichinde virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR, wherein the recombinant arenavirus is Chapare virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Pichinde virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the intergenic region of the L-IGR has been substituted with an S-IGR segment intergenic region, wherein the recombinant arenavirus is Amapari virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Pichinde virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Oliveros virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Pichinde virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Cupixi virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Pichinde virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Tamiami virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Pichinde virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Parana virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Pichinde virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Sabia virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Pichinde virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Patawa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Pichinde virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Pirital virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pichinde virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Whitewater Arroyo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Pichinde virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Pampa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pichinde virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Bear canyon virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Pichinde virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR segment of the viral genome has been substituted with an S-IGR, wherein the recombinant arenavirus is Tonto Creek virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Pichinde virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Allpahuayo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Pichinde virus, Catarina virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Catarina virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR segment has been substituted with an S-IGR, wherein the recombinant arenavirus is Skinner Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Catarina virus, Real de Catorce virus, Big Brushy Tank virus, or Ocozocoautla de Espinosa virus.

Also, for example, disclosed herein are live attenuated arenavirus vaccines comprising a recombinant arenavirus wherein the L-IGR segment of the viral genome has been substituted with an S-IGR, wherein the recombinant arenavirus is Real de Catorce virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Big Brushy Tank virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Big Brushy Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Catarina virus, or Ocozocoautla de Espinosa virus.

Also, for example, disclosed herein are live attenuated arenavirus vaccines comprising a recombinant arenavirus wherein the L-IGR has been substituted with an S-IGR, wherein the recombinant arenavirus is Ocozocoautla de Espinosa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, or Catarina virus.

In one aspect, the live attenuated arenavirus vaccines comprise a recombinant arenavirus wherein both the recombinant arenavirus and the virus from which the S-IGR that replaced the L segment IGR is derived are both Old World arenaviruses or both New World arenaviruses; or wherein the recombinant arenavirus is an Old World arenavirus and the S-IGR is derived from a New World arenavirus; or wherein the recombinant arenavirus is an New World arenavirus and the S-IGR is derived from an Old World arenavirus.

It is also disclosed and herein contemplated that the S-IGR of the live attenuated vaccines disclosed herein can be synthetically derived (i.e., a synthetic sequence with S-like features). Thus, for example, disclosed herein are live attenuated arenavirus vaccines comprising a recombinant arenavirus, wherein the L-IGR is substituted with an S-IGR, and wherein the S-IGR that is replacing the L-IGR comprises a synthetic sequence with S-like features.

It is understood and herein contemplated that the disclosed live attenuated vaccines can be administered to a subject in vivo for the prophylactic or therapeutic treatment of an arenavirus infection or hemorrhagic fever (HF) caused by an arenavirus (for example, Lassa Fever). It is further understood and herein contemplated that the disclosed live arenavirus vaccines can comprise additional immunogenic determinants such as peptides, proteins that induce an immunogenic response to an arenavirus.

It is further contemplated herein that the disclosed live attenuated arenavirus vaccines do not have comprise only one recombinant arenavirus, but can also comprise two or more different recombinant arenaviruses (i.e., a vaccine cocktail). It is contemplated herein that such vaccine cocktails can comprise two, three, four, five, six, seven, eight, nine, ten, or more recombinant viruses of the same species of arenavirus but differing in the S-IGR used to replace the L-IGR and/or different species of arenavirus altogether. For example, the vaccine can comprise a recombinant LCMV and a recombinant Lassa. Also, for example, the vaccine can comprise a Lassa virus with a LCMV S-IGR and a Lassa virus with a synthetic S-IGR. Thus, for example, the live attenuated vaccine can comprise two or more of the a recombinant arenaviruses including, but not limited to, recombinant lymphocytic choriomeningitis virus, recombinant Lassa virus, recombinant Luna virus, recombinant Lujo virus, recombinant Ippy virus, recombinant Mopeia virus, recombinant Mobala virus, recombinant Merino walk virus, recombinant Menekre virus, recombinant Morogoro virus, recombinant Gbagroube virus, recombinant Kodoko virus, recombinant Lemniscomys virus, recombinant Mus minutoides virus, recombinant Lunk virus, recombinant Giaro virus, recombinant Tacaribe virus, recombinant Junin virus, recombinant Machupo virus, recombinant Guanarito virus, recombinant Pichinde virus, recombinant Flexal virus, recombinant Latino virus, recombinant Chapare virus, recombinant Amapari virus, recombinant Oliveros virus, recombinant Cupixi virus, recombinant Tamiami virus, recombinant Parana virus, recombinant Sabia virus, recombinant Patawa virus, recombinant Pirital virus, recombinant Whitewater Arroyo virus, recombinant Pampa virus, recombinant Bear Canyon virus, recombinant Tonto Creek virus, recombinant Allpahuayo virus, recombinant Catarina virus, recombinant Skinner Tank virus, recombinant Real de Catorce virus, recombinant Big Brushy Tank virus, recombinant Catarina virus, and recombinant Ocozocoautla de Espinosa virus; and wherein by recombinant arenavirus is meant an arenavirus that at least comprises a substitution of an L-IGR with an S-IGR.

It is further contemplated herein that the disclosed live attenuated arenavirus vaccines can comprise an adjuvant to increase immunogenicity.

It is also understood and herein contemplated that the disclosed live attenuated arenavirus vaccines can comprise any number of pharmaceutical carriers and agents to facilitate packaging, storage, delivery, administration, or efficacy.

6. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages (i.e., effective amounts) and schedules for administering the compositions may be determined empirically, and making such determinations is within the skill in the art. The dosage ranges for the administration of the compositions are those large enough to produce the desired effect in which the symptoms of the disorder are effected or a protective immune response is induced. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as live attenuated arenavirus vaccine, for treating, inhibiting, or preventing an arenavirus infection (such as, for example a Lassa virus infection), the efficacy of the live attenuated arenavirus vaccine can be assessed in various ways well known to the skilled practitioner. For instance, one of ordinary skill in the art will understand that a composition, such as a live attenuated arenavirus vaccine, disclosed herein is efficacious in treating or inhibiting an arenavirus infection (such as, for example a Lassa virus infection) in a subject by observing that the composition reduces viral load or prevents a further increase in viral load. Viral loads can be measured by methods that are known in the art, for example, using polymerase chain reaction assays to detect the presence of arenavirus nucleic acid or antibody assays to detect the presence of an arenavirus protein in a sample (e.g., but not limited to, blood) from a subject or patient, or by measuring the level of circulating anti-arenavirus antibody levels in the patient. Efficacy of the administration of the disclosed composition may also be determined by measuring the number of arenavirus specific $CD8^+$ T cells, CD4+ T cells, or antibodies in the in an immunized subject. A vaccine treatment that increase the number of arenavirus-specific CD8+ T cells, $CD4^+$ T cells, or antibodies in a subject, is an efficacious arenavirus vaccine treatment.

The compositions that are disclosed herein may be administered prophylactically to patients or subjects who are at risk for arenavirus exposure. In subjects who have been newly exposed to arenavirus (such as, for example Lassa virus) but who have not yet displayed the presence of the virus (as measured by PCR or other assays for detecting the virus) in blood or other body fluid, efficacious treatment with a vaccine partially or completely inhibits the appearance of the virus in the blood or other body fluid.

The compositions disclosed herein and the compositions necessary to perform the disclosed methods can be made using any method known to those of skill in the art for that particular reagent or compound unless otherwise specifically noted.

C. METHOD OF ATTENUATING AN ARENAVIRUS

The disclosure herein provides recombinant arenaviruses that have been attenuated and suitable for use as or as a component of a live attenuated arenavirus vaccine. It is understood and herein contemplated that the methodology used herein to produce the disclosed recombinant virus can be used to make other recombinant arenaviruses and/or other live attenuated vaccines. Thus, in one aspect, disclosed herein are methods of attenuating an arenavirus and/or making a live attenuated arenaviral vaccine comprising substituting the L-IGR with an S-IGR within the arenavirus genome.

It is understood and herein contemplated that the disclosed methods of attenuating an arenavirus and/or making a live attenuated arenaviral vaccine can work with any arenavirus including, but not limited to all known Old World arenaviruses or a New World arenaviruses. For example, in one aspect, disclosed herein are methods of attenuating an arenaviruses or making a live attenuated arenavirus vaccine comprising substituting the intergenic region of the L segment of the arenaviral genome with an S-IGR, wherein the arenavirus is an Old World arenaviruses selected from the group consisting of lymphocytic choriomeningitis virus (LCMV), Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, and Wenzhou virus. Also disclosed are methods of attenuating arenaviruses or making a live attenuated arenaviral vaccine comprising substituting the L-IGR with an S-IGR in the arenavirus genome, wherein the arenavirus is a New World Arenavirus selected from the group consisting of Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus.

As disclosed above, the attenuation methods and/or live attenuated vaccine construction methods comprise substituting the arenavirus L-IGR with an S-IGR. It is understood and herein contemplated that the S-IGR that is replacing the L-IGR can be derived from the same species of arenavirus as the recombinant arenavirus (e.g., a recombinant Lassa virus wherein the viral L-IGR has been substituted with a Lassa virus S-IGR). For example disclosed herein are methods of attenuating an arenavirus or making a live attenuated arenaviral vaccine comprising substituting the L-IGR with an S-IGR, wherein the arenavirus being attenuated and the arenavirus from which the substituting S-IGR is derived are both lymphocytic choriomeningitis virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Alternatively, it is also disclosed and herein contemplated that the S-IGR that is replacing the L-IGR can be derived from a different species of arenavirus than the arenavirus being attenuated (e.g., a recombinant Lassa virus comprising an LCMV S-IGR in the place of the Lassa virus L-IGR). For example, disclosed herein are methods of attenuating an arenavirus or making a live attenuated arenaviral vaccine comprising substituting the L-IGR of the arenaviral genome of the arenavirus with an S-IGR from a different species of arenavirus, wherein the arenavirus being attenuated is LCMV and the S-IGR is derived from Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR of the arenaviral genome of the arenavirus with an S-IGR from a different species of arenavirus, wherein the arenavirus being attenuated is Lassa virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Luna virus and the S-IGR is derived from LCMV virus, Lassa virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Lujo virus and the S-IGR is derived from LCMV virus, Luna virus, Lassa virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Ippy virus and the S-IGR is derived from LCMV virus, Luna virus, Lujo virus, Lassa virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Mopeia virus and the S segment IGR is derived from LCMV virus, Luna virus, Lujo virus, Ippy virus, Lassa virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Mobala virus and the S-IGR is derived from LCMV virus, Luna virus, Lujo virus, Ippy virus, Mopeia virus, Lassa virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Merino walk virus and the S-IGR is derived from LCMV virus, Luna virus, Lujo virus, Ippy virus, Mopeia virus, Mobala virus, Lassa virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Menekre virus and the S-IGR is derived from LCMV virus, Luna virus, Lujo virus, Ippy virus, Mopeia virus, Mobala virus, Merino walk virus, Lassa virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Morogoro virus and the S-IGR is derived from LCMV virus, Luna virus, Lujo virus, Ippy virus, Mopeia virus, Mobala virus, Merino walk virus, Menekre virus, Lassa virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Gbagroube virus and the S-IGR is derived from LCMV virus, Luna virus, Lujo virus, Ippy virus, Mopeia virus, Mobala virus, Merino walk virus, Menekre virus, Morogoro virus, Lassa virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Kodoko virus and the S-IGR is derived from LCMV virus, Luna virus, Lujo virus, Ippy virus, Mopeia virus, Mobala virus, Merino walk virus, Menekre virus, Morogoro virus, Gbagroube virus, Lassa virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Lemniscomys virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lassa virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Mus minutoides virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Lassa virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Lunk virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lassa virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Giaro virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Lassa virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Wenzhou virus and the S-IGR is derived from LCMV virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Lassa virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Junin virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Machupo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Tacaribe virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Guanarito virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Pichinde virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Flexal virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Pichinde virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Latino virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Pichinde virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Chapare virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Pichinde virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Amapari virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Pichinde virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Oliveros virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Pichinde virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Cupixi virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Pichinde virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Tamiami virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Pichinde virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Parana virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Pichinde virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Sabia virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Pichinde virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Patawa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Pichinde virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Pirital virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pichinde virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR segment intergenic region from a different species of arenavirus, wherein the arenavirus being attenuated is Whitewater Arroyo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Pichinde virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Pampa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pichinde virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Bear canyon virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Pichinde virus, Tonto Creek virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Tonto Creek virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Pichinde virus, Allpahuayo virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Allpahuayo virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Pichinde virus, Catarina virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Catarina virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Skinner Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Catarina virus, Real de Catorce virus, Big Brushy Tank virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Real de Catorce virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Big Brushy Tank virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Big Brushy Tank virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Catarina virus, or Ocozocoautla de Espinosa virus.

Also, for example, disclosed herein are methods of attenuating an arenavirus or making a live attenuated arenaviral vaccine comprising substituting the L-IGR with an S-IGR from a different species of arenavirus, wherein the arenavirus being attenuated is Ocozocoautla de Espinosa virus and the S-IGR is derived from LCMV virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Machupo virus, Junin virus, Tacaribe virus, Guanarito virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Pichinde virus, Skinner Tank virus, Real de Catorce virus, Big Brushy Tank virus, or Catarina virus.

In one aspect, disclosed herein are methods of attenuating an arenavirus or making an attenuated vaccine wherein both the arenavirus being attenuated and the virus from which the S-IGR that replaced the L-IGR is derived are both Old World arenaviruses or both New World arenaviruses. Also disclosed are methods where the arenavirus being attenuated is an Old World arenavirus and the S-IGR is derived from a New World arenavirus. Also disclosed are methods wherein the arenavirus being attenuated is a New World arenavirus and the S-IGR is derived from an Old World arenavirus.

It is also disclosed and herein contemplated that the S-IGR that is replacing the L-IGR can be synthetically derived. That is, the substituting S-IGR is a synthetic sequence with S-like features. Thus, for example, disclosed herein are methods of attenuating an arenavirus or making a live attenuated arenaviral vaccine comprising substituting the L-IGR with an S-IGR, wherein the substituting S-IGR is a synthetic sequence with S-IGR like features.

D. METHODS OF TREATING OR PREVENTING AN ARENAVIRAL INFECTION

In one aspect, it is understood and herein contemplated that the live attenuated vaccines described herein can be used in methods of providing a treatment or prophylaxis for infection or conditions caused by arenavirus comprising administering to a subject at risk for exposure to said arenavirus, or alternatively currently infected by said arenavirus, an effective amount of a LAV, thereby inducing an immune response in said subject and thereby providing immune protection against said arenavirus infection. In other words, disclosed herein are methods of immunizing a subject against an arenavirus infection, treating an arenaviral infection, inhibiting an arenaviral infection, and/or preventing an arenaviral infection comprising administering to the subject any of the recombinant arenaviruses or live attenuated vaccines disclosed herein, wherein the recombinant arenavirus being administered individually or as a component of a live attenuated vaccine is derived from the same species of arenavirus as the arenavirus being targeted for treatment, inhibition, immunization, or prevention. Thus, for example, disclosed herein are methods immunizing a subject against an arenavirus infection, treating an arenaviral infection, inhibiting an arenaviral infection, and/or preventing an arenaviral infection wherein both the recombinant virus or recombinant virus in a live attenuated arenaviral vaccine and the arenavirus being targeted for treatment, inhibition, immunization, or prevention are both lymphocytic choriomeningitis virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, Wenzhou virus, Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, or Ocozocoautla de Espinosa virus.

As used herein the terms treatment, treat, or treating refers to a method of reducing one or more of the effects of the infection or one or more symptoms of the infection by eliciting an immune response in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an infection is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection or disease or symptoms of the infection or disease.

As used herein, the terms prevent, preventing, and prevention of an infection, refers to an action, for example, administration of a therapeutic agent (e.g., a composition disclosed herein), that occurs before or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%>, 20%>, 30%>, 40%>, 50%>, 60%>, 70%), 80%), 90%) or greater relative to a control level. For example, the disclosed methods are considered to be a prevention if there is about a 10%> reduction in onset, exacerbation or recurrence of infection, or symptoms of infection in a subject exposed to an infection when compared to control subjects exposed to an infection that did not receive a composition for decreasing infection. Thus, the reduction in onset, exacerbation or recurrence of infection can be about a 10, 20, 30, 40, 50, 60, 70, 80, 90, 100%, or any amount of reduction in between as compared to control subjects. For example, and not to be limiting, if about 10% of the subjects in a population do not become infected as compared to subjects that did not receive preventive treatment, this is considered prevention. Similarly, as used herein, "inhibit" or "inhibition" refers to any decreased change in viral growth, replication, or spread that decreases the virulence of a virus. Inhibition can commence after antigenic exposure. Inhibition can comprise a change of 10%>, 20%>, 30%>, 40%>, 50%>, 60%>, 70%>, 80%>, 90%> or greater relative to a control level. For example, the disclosed methods are considered to be a inhibition if there is about a 10%> reduction in onset, exacerbation, or recurrence of infection, replication rate of a virus, viral spread, or symptoms of infection in a subject exposed to an infection when compared to control subjects exposed to an infection that did not receive a composition for decreasing infection.

It is further understood and herein contemplated that many conditions resulting from arenaviral infections can be the result of the T cell response to the virus rather than the infecting virus itself. Accordingly, there are instances wherein a recombinant virus or vaccine comprising a recombinant arenavirus being used as a treatment for an ongoing arenaviral infection have been further modified to remove one or more T cell epitopes such as immunodominant or subdominant CD8+ T cell epitopes. Thus, disclosed herein are methods of treating a arenaviral infection or condition resulting from an arenaviral infection, comprising administering to a subject an effective amount of any of the recombinant arenaviruses or live attenuated vaccines disclosed herein; wherein the recombinant arenavirus or recombinant arenavirus being used as part of the live attenuated vaccine has been further modified to remove one or more CD8+ T cell epitopes.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Reorganization of LCMV a) Results

(1) LCMV S- and L-IGR have Distinct Functions

For a given arenavirus its S- and L-IGR differ in both sequence and predicted structure (FIG. 1A). To examine whether these differences were associated with distinct functional roles in virus multiplication an attempt was made to rescue recombinant LCM viruses with different IGR combinations (FIG. 1B). In addition to the wild type (WT) rLCMV(IGR/S-L), rLCMV(IGR/S-S) was also rescued where the S-IGR substituted for the L-IGR. In contrast, the other two possible IGR combinations, rLCMV(IGR/L-L) and rLCMV(IGR/L-S) resulted in non-viable viruses, indicating that the S- and L-IGR have distinct functions. The rLCMV(IGR/S-S) grew to high titers in cultured cells but, compared to rLCMV WT, exhibited a moderate decrease in fitness (FIG. 1C), which was associated with the production of high levels of novel L segment-derived RNA species of genome polarity (FIG. 1D, asterisk).

(2) Characterization In Vivo of rLCMV(IGR/S-S)

Figures 3, 4, 5:
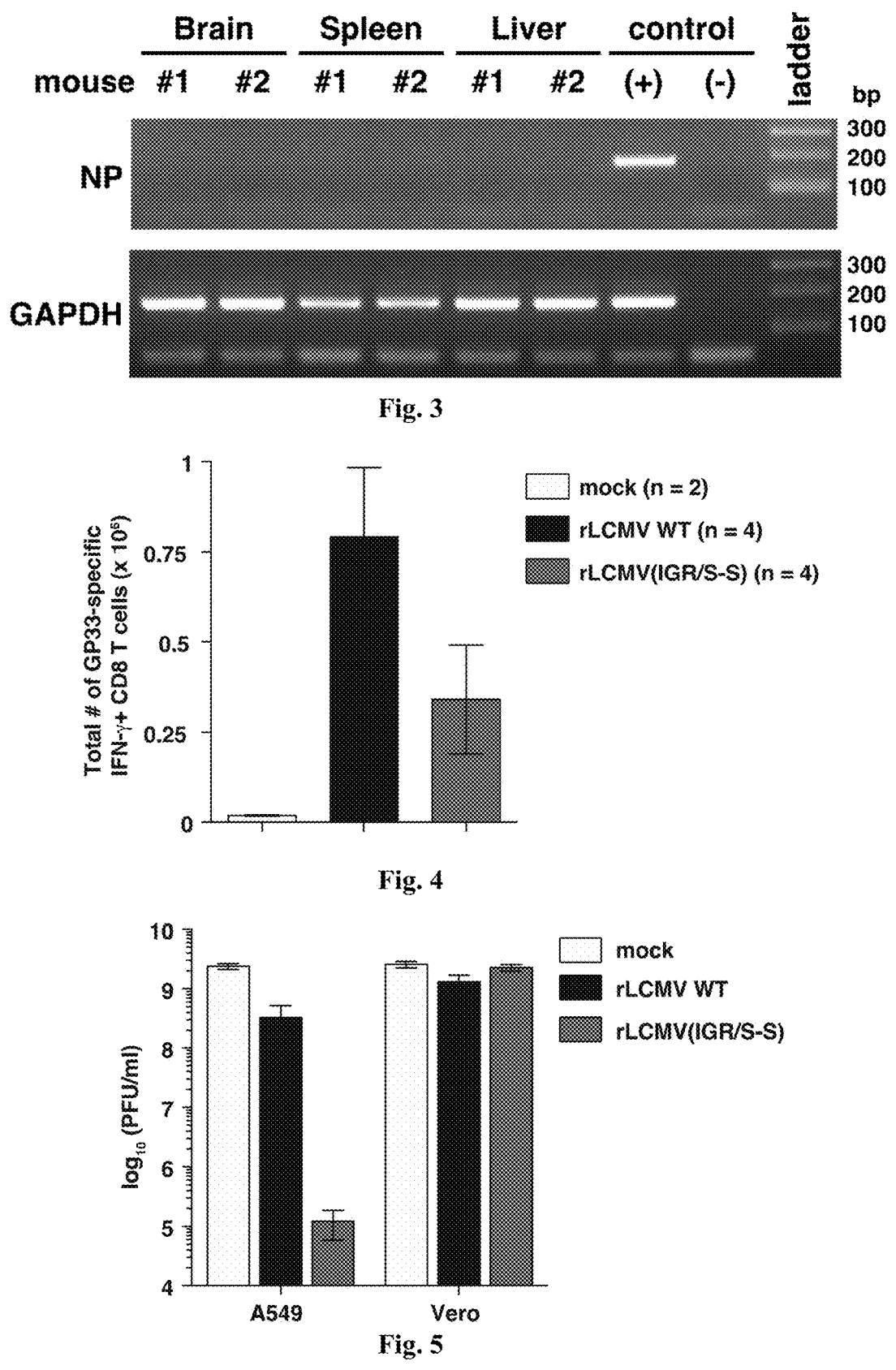
Figure 6:
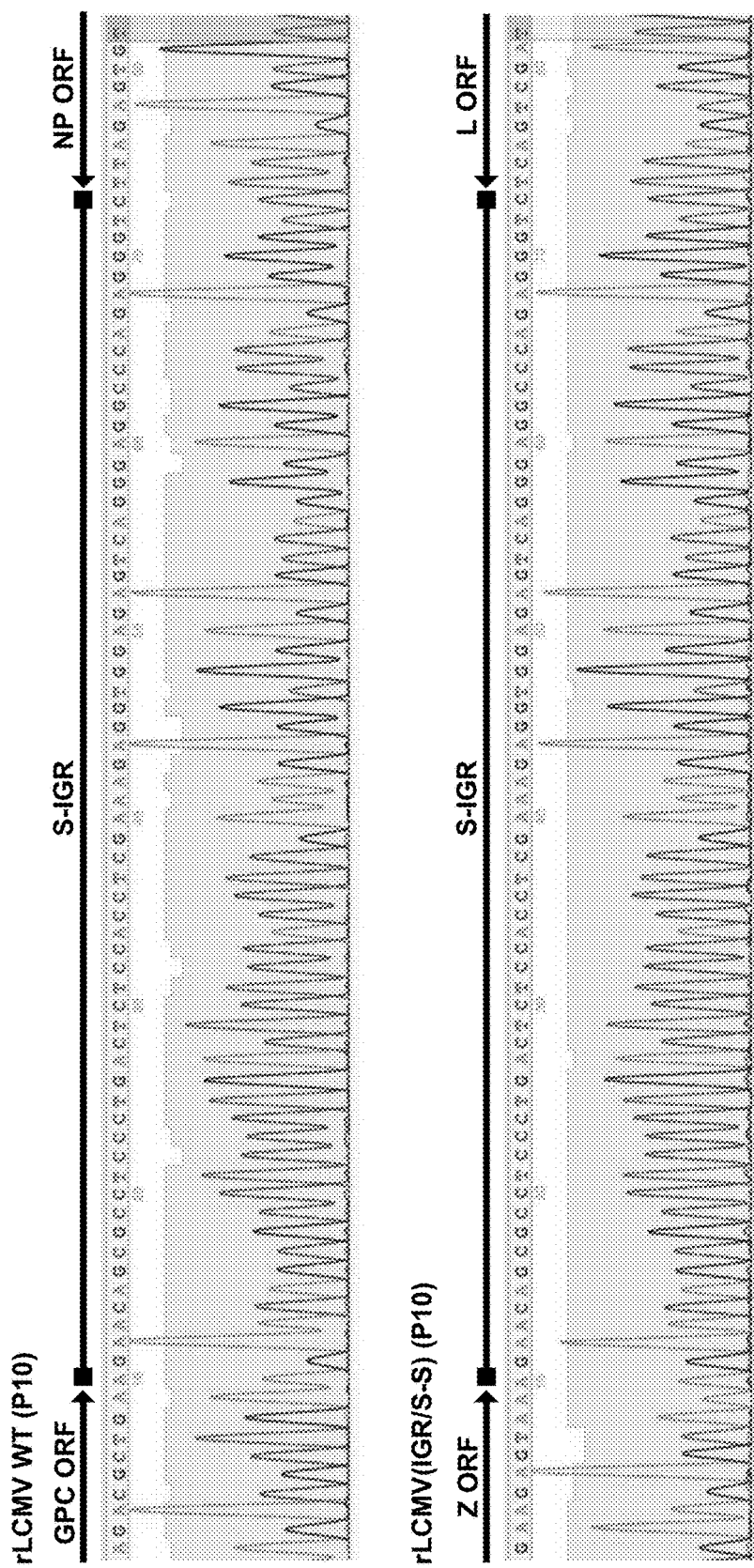

To exam whether the slight decrease in fitness in cultured cells had a significant impact on virulence of rLCMV(IGR/S-S) in vivo, six week-old WT B6 mice were inoculated intracranially (i.c.) with $10^3$ FFU of rLCMV WT or rLCMV (IGR/S-S) (FIG. 2A). Consistent with previous findings, mice infected with rLCMV WT developed a fatal LCM and succumb within 8 days of infection. In contrast, all mice infected with rLCMV(IGR/S-S) survived and did not exhibit morbidity. Virus titers in blood and brain were lower in rLCMV(IGR/S-S)—than rLCMV WT-infected mice (FIG. 2B), but both rLCMV WT- and rLCMV(IGR/S-S)-infected mice exhibited similar viral antigen distribution within the brain (FIG. 2C). Moreover, rLCMV(IGR/S-S)-infected mice subjected 28 days later to a lethal challenge with rLCMV-WT ($10^3$ FFU, i.c.) were fully protected and did not develop noticeable clinical symptoms (FIG. 2A). These results indicated that in vivo rLCMV(IGR/S-S) replicates to significantly lower levels than rLCMV WT, but enough to trigger a protective host immune response. To further confirm this observation rLCMV(IGR/S-S) was used in a standard LCMV immunization protocol by inoculating mice intraperitoneally (i.p.) with $10^5$ FFU. As has been previously extensively documented for mice immunized i.p. with rLCMV WT, six weeks after immunization virus could not be detected in serum and tissues of mice immunized with rLCMV(IGR/S-S) (FIG. 3), but all of them were protected against a lethal challenge with rLCMV WT (i.c., $10^3$ FFU) (FIG. 2D). Protection against fatal LCM disease in mice immunized with rLCMV(IGR/S-S) correlated with a robust CTL response to immunodominant H-2Db-restricted LCMV T-cell epitopes (FIG. 2E and FIG. 4). Consistent with its attenuated in vivo phenotype, rLCMV(IGR/S-S) was significantly impaired, compared to rLCMV WT, in its ability to grow in type I interferon (IFN-I) competent A549 cells (FIG. 2F) and failed to prevent induction of IFN-I by A549 cells (FIG. 2G and FIG. 5). A major concern with LAV is that lack of genetic stability raises the potential for reversion to more virulent forms during multiplication in infected cells. The growth properties of rLCMV(IGR/S-S) and its S-IGR sequence within the L segment did not change during serial passages in BHK-21 cells (FIG. 2H and FIG. 6). Together these results indicated that rLCMV(IGR/S-S) has the key features of a safe and effective LAV: i) growth to high levels in cultured cells, ii) highly attenuated phenotype in vivo but able to elicit protective immunity against a lethal challenge with wild type LCMV, and iii) genetically stable.

(3) Molecular Bases of rLCMV(IGR/S-S) Attenuation

Figure 8A:
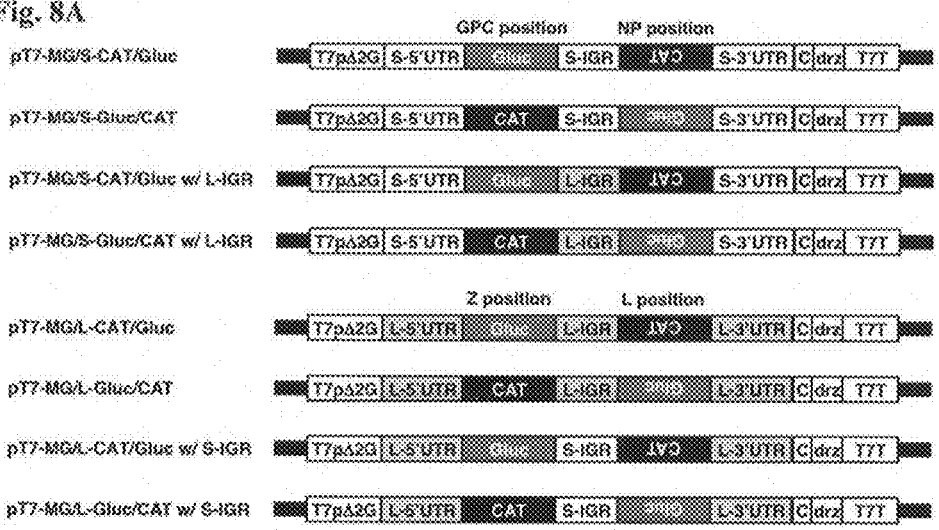

To gain insights about the mechanisms underlying rLCMV(IGR/S-S) attenuation, an investigation was made into the possibility that the L- and S-IGR differed in how they influence viral gene expression, and thereby the replacement of the L-IGR by the S-IGR resulted in a stable altered regulation of virus gene expression that contributed to attenuation. As with other negative strand RNA viruses, LCMV exhibited asymmetric RNA replication and both S and L vRNA species were produced at significant higher levels than the corresponding cRNA species (FIGS. 7A, 7B and 7C). However, levels of GPC and NP mRNAs were rather similar (FIGS. 7B and 7C), which would appear to be in conflict with the well-documented higher levels of NP protein expression compared to GP1 and GP2 proteins. Because of their ambisense coding strategy arenaviruses use same promoter sequence for both viral RNA replication and mRNA transcription, which may pose problems for controlling viral gene expression at the transcriptional level. It was therefore considered that post-transcriptional regulatory events mediated by the IGR can contribute to these apparent discrepancies. To investigate this consideration, an LCMV minigenome (MG) rescue system was used, where the open reading frames (ORF) of the chloramphenicol acetyltransferase (CAT) and *Gaussia* luciferase (Gluc) reporter genes substituted for the viral NP and GPC, respectively, ORFs in the S segment (S-MG), or the Z and L, respectively, ORFs in the L segment (L-MG) (FIG. 9 and FIG. 8A). With this approach the same mRNA and protein can be produced from different loci in the LCMV genome, which allowed for the accurate assessment of the contribution of transcriptional and post-transcriptional regulatory events to gene expression. Reporter gene expression levels were significantly higher when CAT or Gluc where expressed from the NP, compared to GPC, locus in the S-MG (FIG. 9Ai), or from the Z, compared to L, locus in the L-MG (FIG. 9Bi). The location of the CAT ORF in the S-MG had only very modest effects on levels of CAT mRNA expression (FIG. 9Aii), whereas for the L-MG, and as anticipated from the gene expression data, levels of CAT mRNA were higher when CAT was expressed from the Z, compared to L, locus (FIG. 9Bii). These results indicated that the S- and L-IGR play important and distinct roles in post-transcriptional control of viral gene expression. To further investigate this issue, gene expression directed by S-MG(IGR-L) and L-MG(IGR-S) was examined, where the L- and S-IGR substituted for the S- and L-IGR, respectively (FIGS. 9C and 9D). Both S-MG (IGR-L) and L-MG(IGR-S) exhibited reversed gene reporter expression patterns compared to the S-MG (FIG. 9Ci) and L-MG (FIG. 9Di), respectively. One exception was that in L-MG(IGR-S), CAT expression from the Z locus was still slightly (37%) higher than that from the L locus. In contrast, RNA expression patterns were not affected (FIGS. 9Cii and 9Dii). Together, these results indicated that the IGRs regulates arenavirus gene expression at the posttranscriptional level, and decreased expression levels of NP or high expression levels of GPC, or both, might have prevented the production of viable rLCMV(IGR/L-L) and rLCMV(IGR/L-S), whereas a stable altered regulation of Z and L protein expression levels contributed to the attenuation of rLCMV (IGR/S-S).

Figure 8B:
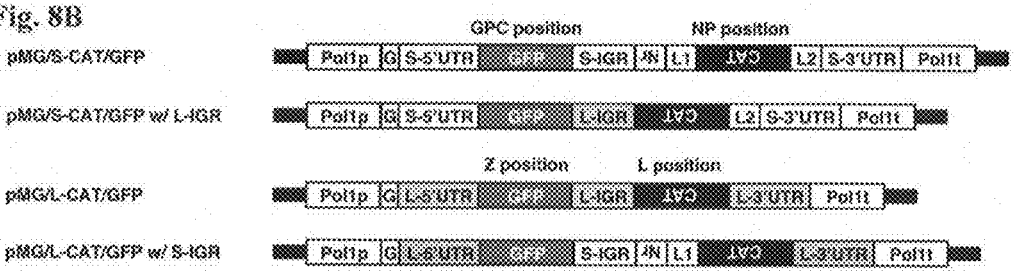
Figure 10A:
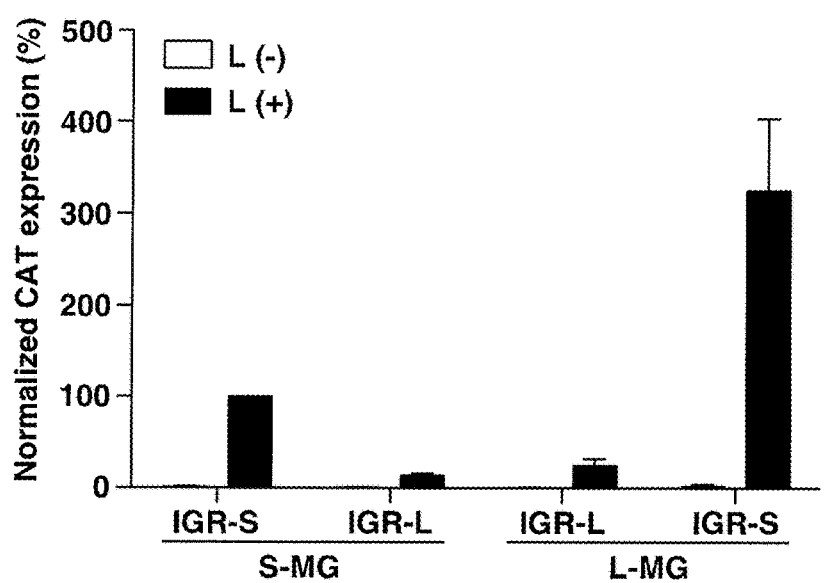
Figure 10B:
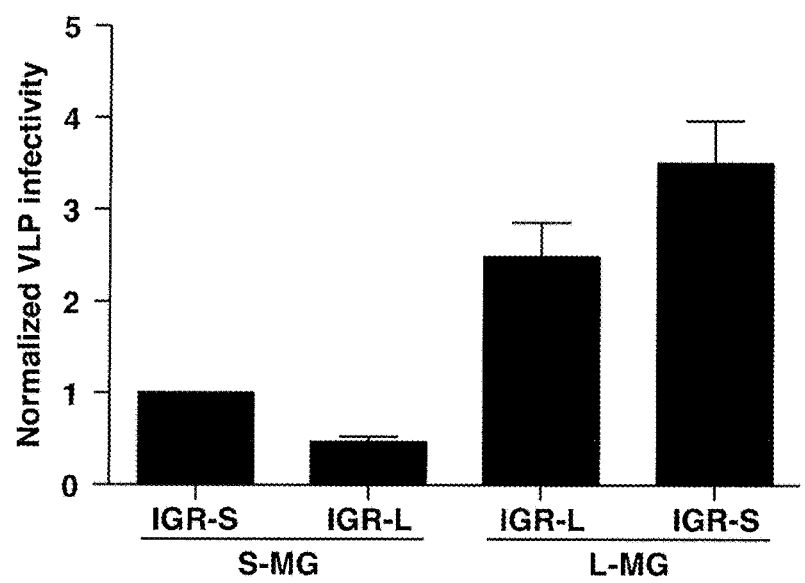
Figure 11:
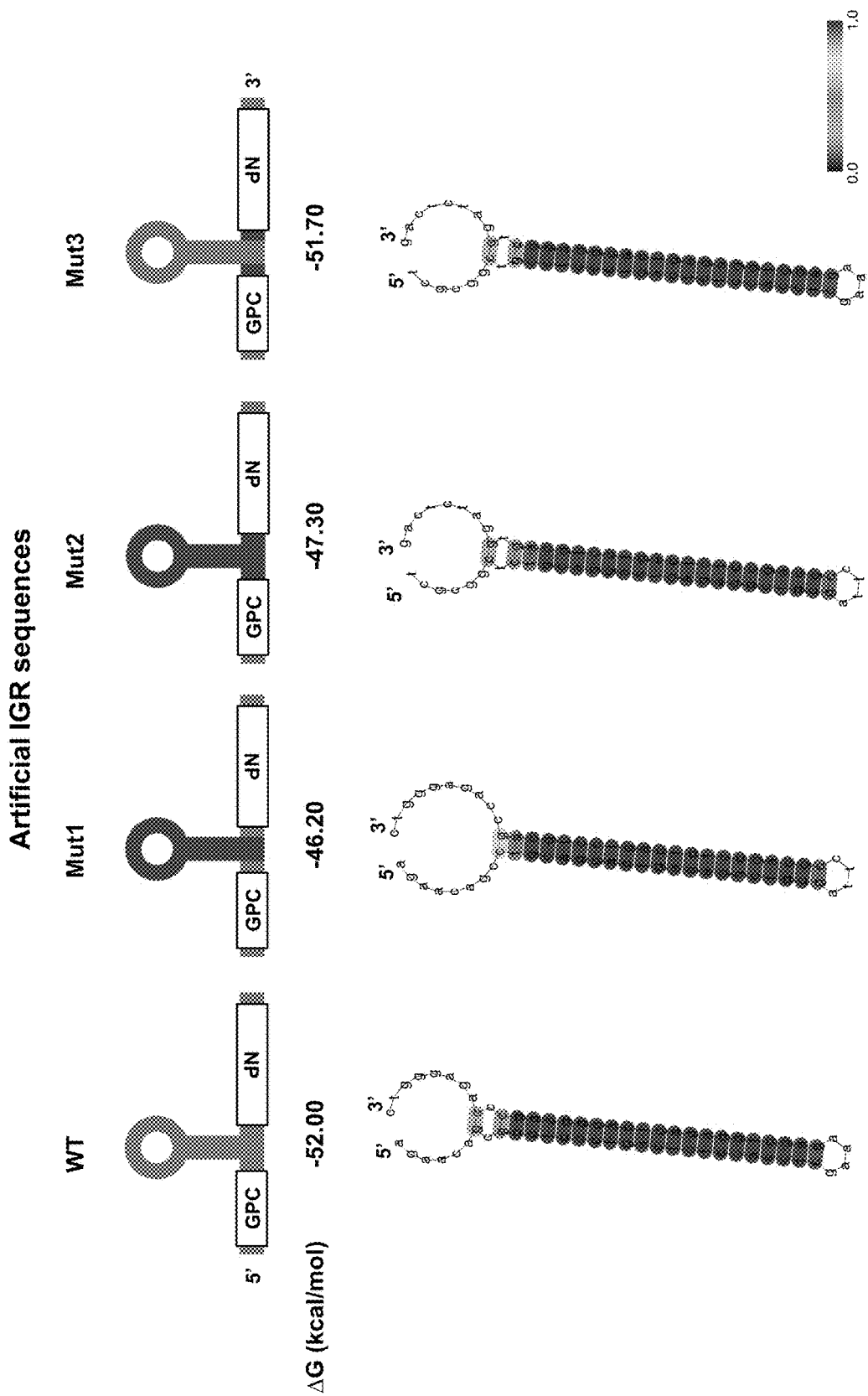
FIG. 11 shows the secondary structure and sequence of three synthetic S-IGRs: Mut1 (SEQ ID NO: 7), Mut2 (SEQ ID NO: 8), and Mut3 (SEQ ID NO: 9) relative to the native LCMV S-IGR (SEQ ID NO: 1) sequence and secondary structure.

The IGR is critical for the production of infectious VLP, but whether the L- and S-IGR differentially contribute to the production of infectious particles was previously unknown. It was therefore reasoned that substitution of the IGR-S for the IGR-L could have negatively impacted the efficiency of production of infectious particles. To examine this question, a collection of MG constructs (FIG. 8B) were generated where GFP was placed in the GPC (S-MG) or Z (L-MG) loci, and CAT was placed in the NP (S-MG) or L (L-MG) loci, and the 3' and 5' UTR, as well as IGRs, were present in all possible combinations (FIG. 8B). Consisting with previous observations, CAT expression from the NP locus was decreased when the L-IGR replaced the S-IGR in the S-MG, whereas CAT expression from the L locus increased when the S-IGR replaced the L-IGR in the L-MG (FIG. 10A). In contrast, the efficiency of S- and L-MG in production of infectious virus-like particles (VLPs) was not significantly affected by the type of IGR present in the MG (FIG. 10B), whereas it was shown that in the absence of IGR production of infectious VLPs was abrogated. Intriguingly, the L-MG was about twice as efficient in production of infectious VLPs compared to S-MG, which might reflect a need to counteract an increased difficulty of incorporating the L virus ribonucleoprotein (vRNP) into virions due to the L genome being about twice the size of the S RNA.

b) Materials and Methods (1) Plasmids

Protein expressing plasmids: pCAGGS-NP (pC-NP), pCAGGS-L (pC-L), pCAGGS-GPC (pC-GPC), pCAGGS-LCMV-Zflag (pC-Z-FLAG), and pCAGGS-T7 have been described. Minigenome (MG) RNA expressing RNA: LCMV MG constructs under control of a modified T7 promoter were generated by PCR based mutagenesis. To generate LCMV S RNA MG constructs, DNA fragments containing the *Gaussia* luciferase (Gluc) and chloramphenicol acetyltransferase (CAT) genes were amplified by PCR and inserted into GPC and NP positions (pT7-MG/S-CAT/Gluc) or NP and GPC positions (pT7-MG/S-Gluc/CAT) of pT7#7Δ2G. LCMV L RNA MG constructs were generated using pT7#7Δ2G as a backbone but the 3'- and 5'UTR and L IGR sequences substituted for the corresponding S genome segment sequences. pT7-MG/L-CAT/Gluc and pT7-MG/L-Gluc/CAT contain the ORFs of Gluc and CAT in Z and L positions, and L and Z positions, respectively. To generate p-T7MG/S-Gluc/CAT w/ L-IGR and pT7-MG/S-CAT/Gluc w/ L-IGR, the S-IGR in pT7-MG/S-Gluc/CAT and pT7-MG/S-CAT/Gluc was replaced with the L IGR. To generate pT7-MG/L-Gluc/CAT w/ S-IGR and pT7-MG/L-CAT/Gluc w/ S-IGR, the L-IGR in pT7-MG/L-Gluc/CAT and pT7-MG/L-CAT/Gluc was replaced with the S IGR. LCMV MG constructs under control of the mouse PolI promoter were generated by PCR based mutagenesis. pMG/S-CAT/GFP has been described. The region containing the S IGR of pMG/S-CAT/GFP was replaced with LCMV L IGR to generate pMG/S-CAT/GFP w/ L-IGR, respectively. pMG/L-CAT/GFP was generated by inserting GFP and CAT genes instead of Z and L genes, respectively, in the pPolIL plasmid. To generate pMG/L-CAT/GFP w/ S-IGR, the L IGR of pMG/L-CAT/GFP was replaced with the S-IGR of pMGS-CAT/GFP. Schematic diagrams of MG constructs used in this study are shown in FIG. 8. Plasmids for rescue of recombinant LCM viruses: Plasmids for rLCMV rescue were generated based on pPolIS ARM and pPolIL ARM plasmids that direct mouse PolI-mediated intracellular synthesis of LCMV S and L RNA genome species of Armstrong (ARM) strain of LCMV. The IGR of pPolIS ARM and pPolIL ARM was replaced with LCMV L IGR and S IGR, respectively to generate pPolIS w/ L-IGR and pPolIL w/ S-IGR, respectively.

(2) Cells and Viruses

BHK-21, Vero, A549, and 293T cells were grown in Dulbecco's modified Eagle's medium (DMEM) (Invitrogen) containing 10% fetal bovine serum (FBS), 2 mM L-glutamine, 100 mg/ml streptomycin, and 100 U/ml penicillin at 37 C and 5% $CO_2$. Recombinant LCMVs used in this study were generated as described with minor modification. BHK-21 cells seeded at $7.5\times10^5$ cells/M6 and cultured overnight were transfected with plasmids directing expression of recombinant S and L RNA genome species (0.8 µg and 1.4 µg of pPolIS and pPolIL, respectively), together with plasmids expressing the viral trans-acting factors NP (0.8 µg of pC-NP) and L (1.0 µg of pC-L) using 10 µl of Lipofectamine 2000 (Invitrogen). After 5 h transfection, tissue culture supernatant (TCS) containing transfection mix was removed and fresh medium added. At three days posttransfection, TCS was removed, 3 ml of fresh medium were added, and cells cultured for another three days. The TCS at six days posttransfection was designated as P0. Rescued viruses were amplified by infection of BHK-21 cells (moi=0.01). At 72 h p.i., TCS collected and clarified by centrifugation at 400 g at 4° C. for 5 min to remove cell debris and stored at −80° C. Either passage 1 or 2 (P1 or P2) were used for experiments.

(3) Virus Titration

LCMV titers were determined using an immunofocus assay as described. Briefly, 10-fold serial virus dilutions were used to infect Vero cell monolayers in a 96-well plate and at 20 h p.i., cells were fixed with 4% paraformaldehyde (PFA) in PBS. After cell permeabilization by treatment with 0.3% Triton X-100 in PBS containing 3% BSA, cells were stained using an anti-NP antibody (VL-4, Bio X Cell) and an Alexa Fluor 568-labeled anti-rat IgG secondary antibody.

(4) Infectious Virus Like Particle (VLP) Assay

Generation of VLPs has been described. BHK-21 cells seeded at $3.5\times10^5$/M12 and cultured overnight were transfected with 0.25 µg of MG expressing plasmid under control of murine PolI, 0.4 µg of pC-NP, 0.5 µg of pC-L, 0.2 µg of pC-GPC, and 50 ng of pC-Z-FLAG using 3.5 µl of Lipofectamine 2000. An empty pCAGGS was used instead of pC-L as negative control (L(−)). 5 h later, TCS containing transfection mix was removed and the cells were cultured in 1.5 ml of fresh medium at 37 C and 5% $CO_2$ for 67 h. Then TCS was collected, clarified by centrifugation at 400 g and 4° C. for 5 min to remove cell debris and 300 µl of clarified TCS used to infect fresh monolayer of BHK-21 cells. At 2 h p.i. with VLPs, cells were superinfected with rLCMV WT (moi=2) to supply trans-acting NP and L protein for RNA replication and expression of the MG RNA delivered by VLPs. After 90 min adsorption, virus inoculum was removed and cells cultured in fresh medium for 72 h. CAT expressions in transfected cells (1st) and VLP-infected cells (2nd) were measured by ELISA. VLP infectivity was determined by dividing 2nd CAT expression with 1st CAT expression.

(5) Growth Kinetics

Cells were infected with rLCMVs for 1 h at the indicated moi. At several times p.i., TCS were collected and viral titers determined using an immunofocus assay. In some experiments, total cellular RNA was isolated using TRI Reagent (Molecular Research Center, Inc.) according to the manufacturer's instructions and used for Northern blotting.

(6) LCMV Minigenome (MG) Assay

LCMV MG assay was done as described. 293T cells seeded in a 12-well plate at $4.5\times10^5$ cells per well and cultured overnight were transfected with 0.5 μg of MG plasmid under control of T7 polymerase, 0.5 μg of pCAGGS-T7, 0.3 μg of pC-NP, and 0.3 μg of pC-L, using 4 μl of Lipofectamine 2000 for 5 h. TCS was removed and the cells cultured in fresh medium for three days. At 72 h posttransfection, TCS was collected to measure *Gaussia* luciferase activity using Biolux *Gaussia* Luciferase Assay Kit (NEW ENGLAND BioLabs), and cells collected using Cell Dissociation Solution Non-enzymatic (SIGMA). Half of the cells were used to determine CAT protein expression using a CAT ELISA kit (Roche), and the other half used to isolate total cellular RNA using TRI Reagent according to the manufacturer's instructions and used for Northern blotting.

(7) Northern Blotting

Total cellular RNA was isolated using TRI Reagent according to the manufacturer's instructions and analyzed by Northern blot hybridization. RNA samples were fractionated by 2.2 M formaldehyde-agarose (1.2%) gel electrophoresis followed by transfer in 20×SSC [3 M sodium chloride, 0.3 M sodium citrate] of the RNA to a Magnagraph membrane using the rapid downward transfer system (TurboBlotter). Membrane-bound RNA was cross-linked by exposure to UV, and the membrane was hybridized to a $^{32}P$-labeled strand-specific probe to genome and/or mRNA species as indicated in figure legends. In the experiment corresponding to figure S6, ribo-probes were used in combinations (NP anti-sense and GPC anti-sense probes and Z sense and Z anti-sense probes) that had similar specific activities to be able to compare signals between two membranes that were exposed the same time in each combination.

(8) Immunization and LCMV Lethal Challenge of Mice

B6 mice (6-week old immunocompetent males) were infected intracranially (i.c.) ($10^3$ FFU) or intraperitoneally (i.p.) ($10^5$ FFU) with the indicated rLCMVs or mock-infected (PBS). Mice were monitored daily for development of clinical symptoms and survival. Lethal LCMV challenge of immunized mice was done by i.c. infection with $10^3$ FFU of rLCMV WT.

All animal experiments were done under protocol 09-0137 approved by The Scripps Research Institute IACUC.

(9) Specific T-Cell Response to LCMV-Immune Dominant Peptide

Adult (6-week old) B6 mice were infected i.p. with $10^5$ FFU of rLCMV WT or rLCMV(IGR/S-S) or mock-infected (PBS). At 28 days p.i., splenocytes were stimulated with 2 μg/ml of MHC class I restricted LCMV-GP33-41 peptide for 1 h in the absence of brefeldin A and then 5 h in the presence of 4 μg/ml brefeldin A. Antibodies to CD3, CD4, and CD8a were added to cells at dilution of 1:100 in PBS supplemented with 1% fetal bovine serum and 0.05% sodium azide for 20 min for cell surface staining. Cells were then fixed with 4% PFA in PBS, permeabilized with 2% saponin, and intracellular staining was performed with antibody to IFN-g (XMG1.2). Flow cytometric analysis was performed using a BD LSR II (Becton Dickson) and data was analyzed using FlowJo (Tree Star, Inc., Ashland, Oreg.). Absolute number of cells was determined by multiplying the frequency of specific cell populations by the total number of viable cells.

(10) Stability of rLCMV(IGR/S-S)

BHK-21 cells were seeded ($7.5\times10^5$ cells/M6-well) 18 h prior infection with the indicated rLCMVs (moi=0.01). At 72 h p.i., TCS was collected and clarified from cell debris by centrifugation at 400 g at 4° C. for 5 min, and virus titers determined by an immunofocus assay. TCS from P1 was used to infect a fresh monolayer of BHK-21 cells, and the same process repeated for eight serial passages. At P10, total RNA was isolated from infected cells. DNA fragments containing the IGR were amplified by RT-PCR and sequenced.

(11) Virus RNA Detection from Infected Mice Organs

Adult B6 mice were infected with rLCMV(IGR/S-S) by i.p. Six weeks later, total RNA was isolated from brain, spleen, and liver. DNA fragments containing a part of NP and GAPDH genes with expected lengths of 160 bp and 189 bp, respectively, were amplified by RT-PCR. For PCR, primer pairs of 5'-TGGATCATTAAATCTACCCTCA-3' (SEQ ID NO: 24) and 5'-CAACAATTGATCTCACAAGCGA-3' (SEQ ID NO: 25) and 5'-TGGTATCGTGGAAGGACTCATGAC-3' (SEQ ID NO: 26) and 5'-AGTCCAGTGAGCTTCCCGTTCAGC-3' (SEQ ID NO: 27) were used for NP and GAPDH fragments, respectively.

(12) Detection of Viral Antigen in Brain Tissue

Brains from virus-infected (i.e., $10^3$ FFU of rLCMV WT or rLCMV(IGR/S-S)) and mock-infected (PBS) mice were harvested at 6 days p.i. and embedded in OCT cryomolds and stored frozen (−80° C.). Frozen sections (8-μm) were prepared, fixed with 4% PFA in PBS, and permeabilized and blocked with 5% FBS and 0.3% TritonX-100 in PBS for 1 h. Sections were stained for 90 min at room temperature with a rat monoclonal antibody to LCMV NP (VL-4, 1:200 dilution), followed by washes with PBS and then reacted at room temperature with Alexa Fluor 568-conjugated antibody to rat IgG (1:500) for 40 min. After several washes with PBS, sections were mounted using mounting medium containing 4,6-diamidino-2-phenylindole (DAPI). Antibodies were diluted in PBS containing 3% BSA and 0.3% TritonX-100. Sections were observed under a confocal microscope (LSM710, Zeiss) and images collected using a Zeiss software ZEN. The merged images were generated by Adobe Photoshop.

(13) Interferon (IFN) Bioassay

A549 and Vero cells seeded in a 24-well plate at $1.25 \times 10^5$ cells per well and cultured overnight were infected with the indicated rLCMV (moi=0.1). At 24 h p.i., cells were infected with wild type VSV (moi=0.01) for 32 h, VSV titers in TCS were determined by a plaque assay. Then the cells were cultured in fresh medium for another 16 h, and fixed with 4% PFA in PBS and stained with 0.1% crystal violet (w/v) in PBS.

2. Example 2: Reorganization of Lassa Virus (LASV)

It is shown herein that the IGR serves as a bona fide transcription termination signal, but functional viral mRNA species are produced in the absence of the IGR. However, the absence of IGR prevents formation of infectious virus like particles (VLPs), indicating its involvement in virus assembly. The present description illustrates the roles played by viral specific cis-acting RNA sequences in the arenavirus life cycle. It is shown that efficient interaction between the nucleoprotein (NP) and polymerase (L protein) of LCMV requires the presence of virus-specific RNA sequences that not include the IGR. Moreover, a recombinant LCMV containing the LASV, instead of LCMV, S-IGR exhibited growth properties similar to LCMV WT, indicating that structure rather than sequence specificity within the IGR is required for the production of arenavirus infectious progeny. The role of S- and L-IGR interaction in the production or arenavirus infectious progeny is relevant to the present invention.

Genome reorganization of hemorrhagic fever (HF) arenaviruses following the rules learned with the prototypic arenavirus LCMV permit the generation of a LAV to prevent arenaviral HF disease. In particular, reorganization of the Lassa virus (LASV) genome as described herein which is used in the preparation of a LAV to combat Lassa fever (LF). Moreover, a similar approach can be rapidly implemented to develop a LAV for any human pathogenic arenaviruses.

The advantages of the live attenuated vaccine disclosed herein is that, firstly, the LAV based comprises an identical antigenic replicate of the highly pathogenic parental virus, which will ensure an optimal immune response to the vaccine strain. Secondly, the genetic determinants and mechanism of attenuation of the novel vaccine approach are well characterized, whereas for many classic LAV the mechanisms of attenuation remain a matter of discussion.

F. REFERENCES

Battegay, M. 1993. [Quantification of lymphocytic choriomeningitis virus with an immunological focus assay in 24 well plates]. ALTEX 10:6-14.

Cole, G. A., D. H. Gilden, A. A. Monjan, and N. Nathanson. 1971. Lymphocytic choriomeningitis virus: pathogenesis of acute central nervous system disease. Fed Proc 30:1831-41.

Emonet, S. F., L. Garidou, D. B. McGavern, and J. C. de la Torre. 2009. Generation of recombinant lymphocytic choriomeningitis viruses with trisegmented genomes stably expressing two additional genes of interest. Proc Natl Acad Sci USA 106:3473-8.

Flatz, L., A. Bergthaler, J. C. de la Torre, and D. D. Pinschewer. 2006. Recovery of an arenavirus entirely from RNA polymerase I/II-driven cDNA. Proc Natl Acad Sci USA 103:4663-8.

Lee, K. J., I. S. Novella, M. N. Teng, M. B. Oldstone, and J. C. de La Torre. 2000. NP and L proteins of lymphocytic choriomeningitis virus (LCMV) are sufficient for efficient transcription and replication of LCMV genomic RNA analogs. J Virol 74:3470-7.

Lee, K. J., M. Perez, D. D. Pinschewer, and J. C. de la Torre. 2002. Identification of the lymphocytic choriomeningitis virus (LCMV) proteins required to rescue LCMV RNA analogs into LCMV-like particles. J Virol 76:6393-7.

Perez, M., and J. C. de la Torre. 2003. Characterization of the genomic promoter of the prototypic arenavirus lymphocytic choriomeningitis virus. J Virol 77:1184-94.

Perez, M., R. C. Craven, and J. C. de la Torre. 2003. The small RING finger protein Z drives arenavirus budding: implications for antiviral strategies. Proc Natl Acad Sci USA 100:12978-83.

Pinschewer, D. D., M. Perez, and J. C. de la Torre. 2005. Dual role of the lymphocytic choriomeningitis virus intergenic region in transcription termination and virus propagation. J Virol 79:4519-26.

Sanchez, A. B., and J. C. de la Torre. 2006. Rescue of the prototypic Arenavirus LCMV entirely from plasmid. Virology 350:370-80.

Urata, S., J. Yasuda, and J. C. de la Torre. 2009. The z protein of the new world arenavirus tacaribe virus has bona fide budding activity that does not depend on known late domain motifs. J Virol 83:12651-5.

Wherry, E. J., J. N. Blattman, K. Murali-Krishna, R. van der Most, and R. Ahmed. 2003. Viral persistence alters CD8 T-cell immunodominance and tissue distribution and results in distinct stages of functional impairment. J Virol 77:4911-27.

G. SEQUENCES

SEQ ID NO: 1 Lymphocytic choriomeningitis virus (LCMV) S segment IGR:
agaacagcgcctccctgactctccacctcgaaagaggtggagagtcagggaggcccagagggtc SEQ ID NO: 2 Lymphocytic choriomeningitis virus (LCMV) S segment IGR cRNA SEQ ID NO: 3 Lymphocytic choriomeningitis virus (LCMV) IGR-L vRNA SEQ ID NO: 4 Lymphocytic choriomeningitis virus (LCMV) IGR-L cRNA

G. SEQUENCES

SEQ ID NO: 5 rLCMV WT

SEQ ID NO: 6 rLCMV(IGR/S-S)

SEQ ID NO: 7 Synthetic *Lymphocytic choriomeningitis virus* (LCMV) S segment IGR: Mut 1
AGAACAGCCTGCAGGACTGAGAGGCTGCGATTCCGCAGCCTCTCAGTCCTGCAGCC
AGAGGGTC SEQ ID NO: 8 Synthetic *Lymphocytic choriomeningitis virus* (LCMV) S segment IGR: Mut 2
TCGCGGCTCTGCAGGACTGAGAGGCTGCGATTCCGCAGCCTCTCAGTCCTGCAGTGG
ATCTCAG SEQ ID NO: 9 Synthetic *Lymphocytic choriomeningitis virus* (LCMV) S segment IGR: Mut 3
TCGCGGCTGCCTCCCTGACTCTCCACCTCGAAAGAGGTGGAGAGTCAGGAGGCTGG
ATCTCAG SEQ ID NO: 10 *Lymphocytic choriomeningitis virus* (LCMV) L segment IGR:
agcaccatcttcagatggcatcatttctttatgagggaaccatgaaaaattgcctaatgtcctg SEQ ID NO: 11 *Lassa virus* (LASV) S segment IGR:
gacccttgtcagggcccccgtgacccaccgcctattggcggtgggtcacgggggcgtccat SEQ ID NO: 12 *Lujo virus* (LUJV) S segment IGR:
gagtcccaacacagggaccccatgaccgtcactccgctttgcggagtgacggtcatggggtccgtggagac SEQ ID NO: 13 *Mopeia virus* (MOPV) S segment IGR:
gaggggtgccctccagaccctccaccagagggcccccgtgacccaccgccattggcggtgggtcacggggcgtcccct SEQ ID NO: 14 *Mobala virus* (MOBV) S segment IGR:
tgccccaaaaggggggcccccgtgacccaccgccataaggcggtgggtcacgggggcatcctc SEQ ID NO: 15 *Junin virus* (JUNV) S segment IGR:
gacctcctgagggtccccaccagcccgggcactgcccgggctggtgtggccccccagtccgcggcctggccgcggactggggaggc
actgc SEQ ID NO: 16 *Machupo virus* (MACV) S segment IGR:
acacagccaagacccctgccgacccggggcccagcccgggtcggcggggccccccagtccgcggctctgccgcggactggggaggc
actgc SEQ ID NO: 17 *Tacaribe virus* (TCRV) S segment IGR:
gacagcacatttgcgctcccacgcgctttgcccgggccggtgtggccccccgatccgcgttgccgcggatcggggaggcacctgtggtg
cggaagtcttacagc SEQ ID NO: 18 *Guanarito virus* (GTOV) S segment IGR:
tttcatcagccctccagctctgtcggcccggaaacccgggccgacagagcgcccccccagtccgcggcaatgcccgcggactgggagg
gcatctgc SEQ ID NO: 19 *Pichinde virus* (PICV) S segment IGR:
gccctagcctcgacatgggcctcgacgtcactccccaataggggagtgacgtcgaggcctctgaggacttgagc SEQ ID NO: 20 *Chapare virus* (CHPV) S segment IGR:
acttgagtggctcccaacccaccgtcccggggcatagcccgggacggtgcggcctcccagtccgcggcaaatgccgcggactgggagg
gcatgggc SEQ ID NO: 21 *Flexal virus* (FLEV) S segment IGR:
acaccatccccccccactccgccccgacaggggcggagtggggggcgcccccgggatctccaccccccttgggagtggagatccgggg
agcagatgcagc SEQ ID NO: 22 *Whitewater Arroyo virus* (WWAV) S segment IGR:
aatgtcaaccgaggtggcctccaacgctgcacccccttcgggggtgcagcggtggaggcccttttgcagcc SEQ ID NO: 23 Ocozocoautla de Espinosa virus (OCEV) S segment IGR:
aaacctcaggacaacagtctcccaccggcccgggcactgcccggccggtgtggcctcccgatccgcggctgcgccgcggatcggga
aggcaccgtcagtagtgcaggtgctctcac tgt

SEQ ID NO: 24
TGGATCATTAAATCTACCCTCA

SEQ ID NO: 25
CAACAATTGATCTCACAAGCGA

SEQ ID NO: 26
TGGTATCGTGGAAGGACTCATGAC

SEQ ID NO: 27
AGTCCAGTGAGCTTCCCGTTCAGC

G. SEQUENCES

SEQ ID NO: 28 Synthetic Lymphocytic choriomeningitis virus (LCMV) S segment IGR: Ssyn2
TCGCGGCTCTGCAGGACTGAGAGGCTGCGATTCCGCAGCCTCTCAGT
CCTGCAGTGGATCTCAG

What is claimed is:

1. A recombinant arenavirus, wherein the intergenic region of the L segment of the viral genome has been substituted with an arenavirus or synthetic arenavirus S segment intergenic region.

2. The recombinant Arenavirus of claim 1, wherein the recombinant arenavirus is an Old World arenavirus.

3. The recombinant arenavirus of claim 2, wherein the recombinant arenavirus is an Old World Arenavirus selected from the group consisting of lymphocytic choriomeningitis virus, Lassa virus, Luna virus, Lujo virus, Ippy virus, Mopeia virus, Mobala virus, Merino walk virus, Menekre virus, Morogoro virus, Gbagroube virus, Kodoko virus, Lemniscomys virus, Mus minutoides virus, Lunk virus, Giaro virus, and Wenzhou virus.

4. The recombinant arenavirus of claim 1, wherein the recombinant arenavirus is a New World arenavirus.

5. The recombinant arenavirus of claim 4, wherein the recombinant arenavirus is a New World arenavirus selected from the group consisting of Tacaribe virus, Junin virus, Machupo virus, Guanarito virus, Pichinde virus, Flexal virus, Latino virus, Chapare virus, Amapari virus, Oliveros virus, Cupixi virus, Tamiami virus, Parana virus, Sabia virus, Patawa virus, Pirital virus, Whitewater Arroyo virus, Pampa virus, Bear Canyon virus, Tonto Creek virus, Allpahuayo virus, Catarina virus, Skinner Tank virus, Real de Catorce virus, Big Brushy Tank virus, Catarina virus, and Ocozocoautla de Espinosa virus.

6. The recombinant arenavirus of claim 1, wherein the S-IGR that has replaced the L-IGR is from a different species of arenavirus than the recombinant virus.

7. The recombinant arenavirus of claim 1, wherein the S-IGR that has replaced the L-IGR is from the same species of arenavirus as the recombinant virus.

8. The recombinant arenavirus of claim 1, wherein the S-IGR that has replaced the L-IGR is a synthetic S-IGR.

9. A method of eliciting an immune response in a subject against an arenavirus infection comprising administering to the subject the recombinant arenavirus of claim 1.

10. A composition comprising the recombinant arenavirus of claim 1.

11. A method of eliciting an immune response in a subject against an arenavirus infection comprising administering to the subject the recombinant arenavirus of claim 2.

12. A method of eliciting an immune response in a subject against an arenavirus infection comprising administering to the subject the recombinant arenavirus of claim 4.

13. A method of eliciting an immune response in a subject against an arenavirus infection comprising administering to the subject the recombinant arenavirus of claim 6.

14. A method of eliciting an immune response in a subject against an arenavirus infection comprising administering to the subject the recombinant arenavirus of claim 7.

* * * * *

SEQUENCE LISTING

<160> NUMBER OF SEQ ID NOS: 28

<210> SEQ ID NO 1
<211> LENGTH: 64
<212> TYPE: DNA
<213> ORGANISM: Lymphocytic choriomeningitis virus

<400> SEQUENCE: 1
agaacagcgc ctccctgact ctccacctcg aaagaggtgg agagtcaggg aggcccagag    60
ggtc                                                                64

<210> SEQ ID NO 2
<211> LENGTH: 64
<212> TYPE: RNA
<213> ORGANISM: Lymphocytic choriomeningitis virus

<400> SEQUENCE: 2
gacccucugg gccucccuga cucuccaccu cuuucgaggu ggagagucag ggaggcgcug    60
uccu                                                                64

<210> SEQ ID NO 3
<211> LENGTH: 202
<212> TYPE: RNA
<213> ORGANISM: Lymphocytic choriomeningitis virus

<400> SEQUENCE: 3
caccguccgg ccccggcccc gacaaacagc ccagcacaag ggaaccgcac gucgcccaac    60
gcacacagac acagcaccca acacagaaca cgcacacaca cacacacaca cacccacacg   120
cacgcgcccc caccaccggg gggcgccccc ccccgggggg cggcccccg ggagcccggg    180 cggagcccca cggagaugcc ca                                            202

<210> SEQ ID NO 4
<211> LENGTH: 202
<212> TYPE: RNA
<213> ORGANISM: Lymphocytic choriomeningitis virus

<400> SEQUENCE: 4
ugggcaucuc cguggggcuc cgcccgggcu cccgggggc cgccccccgg ggggggcgc     60 ccccggugg uggggcgcg ugcguguggg ugugugugug ugugugugug cguguucugu    120
guugggugcu gugucugugu gcguugggcg acgugcgguu ccguugugcu gggcuguuug   180
ucggggccgg ggccggacgg ug                                            202

<210> SEQ ID NO 5
<211> LENGTH: 82
<212> TYPE: DNA
<213> ORGANISM: Lymphocytic choriomeningitis virus

<400> SEQUENCE: 5
agacgctgaa gaacagcgcc tccctgactc tccacctcga aagaggtgga gagtcaggga    60
ggcccagagg gtcttagagt gt         82

<210> SEQ ID NO 6
<211> LENGTH: 82
<212> TYPE: DNA
<213> ORGANISM: Lymphocytic choriomeningitis virus

<400> SEQUENCE: 6
gaagagtaaa gaacagcgcc tccctgactc tccacctcga aagaggtgga gagtcaggga         60
ggcccagagg gtctcagtcg at         82

<210> SEQ ID NO 7
<211> LENGTH: 64
<212> TYPE: DNA
<213> ORGANISM: Artificial Sequence
<220> FEATURE:
<223> OTHER INFORMATION: mutant IGR

<400> SEQUENCE: 7
agaacagcct gcaggactga gaggctgcga ttccgcagcc tctcagtcct gcagccagag         60
ggtc         64

<210> SEQ ID NO 8
<211> LENGTH: 64
<212> TYPE: DNA
<213> ORGANISM: Artificial Sequence
<220> FEATURE:
<223> OTHER INFORMATION: mutant IGR sequence

<400> SEQUENCE: 8
tcgcggctct gcaggactga gaggctgcga ttccgcagcc tctcagtcct gcagtggatc         60
tcag         64

<210> SEQ ID NO 9
<211> LENGTH: 63
<212> TYPE: DNA
<213> ORGANISM: Artificial Sequence
<220> FEATURE:
<223> OTHER INFORMATION: mutant IGR sequence

<400> SEQUENCE: 9
tcgcggctgc ctccctgact ctccacctcg aaagaggtgg agagtcagga ggctggatct         60
cag         63

<210> SEQ ID NO 10
<211> LENGTH: 64
<212> TYPE: DNA
<213> ORGANISM: Lymphocytic choriomeningitis virus

<400> SEQUENCE: 10
agcaccatct tcagatggca tcatttcttt atgagggaac catgaaaaat tgcctaatgt         60
cctg         64

<210> SEQ ID NO 11
<211> LENGTH: 61
<212> TYPE: DNA
<213> ORGANISM: Lassa virus

<400> SEQUENCE: 11
gacccttgtc agggcccccg tgacccaccg cctattggcg gtgggtcacg ggggcgtcca         60
t         61

<210> SEQ ID NO 12
<211> LENGTH: 71
<212> TYPE: DNA
<213> ORGANISM: lujo virus

<400> SEQUENCE: 12
gagtcccaac acagggaccc catgaccgtc actccgcttt gcggagtgac ggtcatgggg    60
tccgtggaga c                                                        71

<210> SEQ ID NO 13
<211> LENGTH: 80
<212> TYPE: DNA
<213> ORGANISM: Mopeia virus

<400> SEQUENCE: 13 gaggggtgc cctccagacc ctccaccaga gggcccccgt gacccaccgc cattggcggt     60
gggtcacggg ggcgtcccct                                               80

<210> SEQ ID NO 14
<211> LENGTH: 63
<212> TYPE: DNA
<213> ORGANISM: Mobala virus

<400> SEQUENCE: 14
tgccccaaaa ggggggcccc cgtgacccac cgccataagg cggtgggtca cgggggcatc    60
ctc                                                                 63

<210> SEQ ID NO 15
<211> LENGTH: 91
<212> TYPE: DNA
<213> ORGANISM: Junin virus

<400> SEQUENCE: 15
gacctcctga gggtccccac cagcccgggc actgcccggg ctggtgtggc ccccagtcc     60 gcggcctggc cgcggactgg ggaggcactg c                                  91

<210> SEQ ID NO 16
<211> LENGTH: 90
<212> TYPE: DNA
<213> ORGANISM: Machupo virus

<400> SEQUENCE: 16
acacagccaa gacccctgcc gacccgggcc cagcccgggt cggcggggcc ccccagtccg    60
cggctctgcc gcggactggg gaggcactgc                                    90

<210> SEQ ID NO 17
<211> LENGTH: 104
<212> TYPE: DNA
<213> ORGANISM: Tacaribe virus

<400> SEQUENCE: 17
gacagcacat ttgcgctccc acgcgctttg cccgggccgg tgtggccccc cgatccgcgt    60
tgccgcggat cggggaggca cctgtggtgc ggaagtctta cagc                   104

<210> SEQ ID NO 18
<211> LENGTH: 95
<212> TYPE: DNA
<213> ORGANISM: Guanarito virus

```
<400> SEQUENCE: 18
tttcatcagc cctccagctc tgtcggcccg gaaacccggg ccgacagagc gcccccagt      60 ccgcggcaat gcccgcggac tgggagggca tctgc                                95

<210> SEQ ID NO 19
<211> LENGTH: 74
<212> TYPE: DNA
<213> ORGANISM: Pichinde virus

<400> SEQUENCE: 19
gccctagcct cgacatgggc ctcgacgtca ctccccaata ggggagtgac gtcgaggcct      60
ctgaggactt gagc                                                        74

<210> SEQ ID NO 20
<211> LENGTH: 95
<212> TYPE: DNA
<213> ORGANISM: chapare virus

<400> SEQUENCE: 20
acttgagtgg ctcccaaccc accgtcccgg gcatagcccg ggacggtgcg gcctcccagt      60
ccgcggcaaa tgccgcggac tgggagggca tgggc                                95

<210> SEQ ID NO 21
<211> LENGTH: 98
<212> TYPE: DNA
<213> ORGANISM: Flexal virus

<400> SEQUENCE: 21
acaccatccc ccccactcc gccccgacag gggcggagtg gggggcgccc cgggatctcc       60 accccttgg gagtggagat ccggggagca gatgcagc                              98

<210> SEQ ID NO 22
<211> LENGTH: 71
<212> TYPE: DNA
<213> ORGANISM: Whitewater Arroyo virus

<400> SEQUENCE: 22
aatgtcaacc gaggtggcct ccaacgctgc accccttcg ggggtgcag cggtggaggc        60 cctttgcagc c                                                           71

<210> SEQ ID NO 23
<211> LENGTH: 120
<212> TYPE: DNA
<213> ORGANISM: Ocozocoautla de Espinosa virus

<400> SEQUENCE: 23
aaacctcagg acaacagtct cccaccggcc cgggcactgc ccgggccggt gtggcctccc      60
gatccgcggc tgcgccgcgg atcgggaagg caccgtcagt agtgcaggtg ctctcactgt     120

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tggatcatta aatctaccct ca                                               22
```

```
<210> SEQ ID NO 25
<211> LENGTH: 22
<212> TYPE: DNA
<213> ORGANISM: artificial sequence
<220> FEATURE:
<223> OTHER INFORMATION: primer

<400> SEQUENCE: 25
caacaattga tctcacaagc ga                                              22

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
tggtatcgtg gaaggactca tgac                                            24

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
agtccagtga gcttcccgtt cagc                                            24

<210> SEQ ID NO 28
<211> LENGTH: 64
<212> TYPE: DNA
<213> ORGANISM: Artificial Sequence
<220> FEATURE:
<223> OTHER INFORMATION: synthetic sequence

<400> SEQUENCE: 28
tcgcggctct gcaggactga gaggctgcga ttccgcagcc tctcagtcct gcagtggatc     60
tcag                                                                  64
```